US010976321B2

(12) United States Patent
Schulz-Knappe et al.

(10) Patent No.: US 10,976,321 B2
(45) Date of Patent: *Apr. 13, 2021

(54) MASS SPECTROMETRIC QUANTITATION

(71) Applicant: Electrophoretics Limited, Surrey (GB)

(72) Inventors: Peter Schulz-Knappe, Frankfurt-am-Main (DE); Ian Pike, Surrey (GB); Karsten Kuhn, Hofheim Am Taunus (DE)

(73) Assignee: ELECTROPHORETICS LIMITED, London (GB)

(*) Notice: Subject to any disclaimer, the term of this patent is extended or adjusted under 35 U.S.C. 154(b) by 392 days.

This patent is subject to a terminal disclaimer.

(21) Appl. No.: 15/412,555

(22) Filed: Jan. 23, 2017

(65) Prior Publication Data

US 2017/0146544 A1 May 25, 2017

Related U.S. Application Data

(63) Continuation of application No. 14/697,455, filed on Apr. 27, 2015, now abandoned, which is a continuation of application No. 12/530,747, filed as application No. PCT/EP2008/052962 on Mar. 12, 2008, now abandoned.

(30) Foreign Application Priority Data

Mar. 12, 2007 (GB) .................................... 0704764

(51) Int. Cl.
| | | |
|---|---|---|
| G01N 33/53 | (2006.01) | |
| G01N 1/28 | (2006.01) | |
| G01N 33/58 | (2006.01) | |
| G01N 33/68 | (2006.01) | |
| H01J 49/00 | (2006.01) | |
| G01N 33/96 | (2006.01) | |

(52) U.S. Cl.
CPC ............ *G01N 33/58* (2013.01); *G01N 1/28* (2013.01); *G01N 33/6848* (2013.01); *G01N 33/6851* (2013.01); *G01N 33/96* (2013.01); *H01J 49/0009* (2013.01); *G01N 2001/2893* (2013.01); *G01N 2333/4703* (2013.01); *G01N 2333/765* (2013.01); *G01N 2333/775* (2013.01); *G01N 2458/15* (2013.01); *G01N 2560/00* (2013.01); *G01N 2570/00* (2013.01); *Y10T 436/105831* (2015.01)

(58) Field of Classification Search
CPC ........... G01N 33/6848; G01N 33/6851; G01N 33/58; G01N 1/28; G01N 33/96; G01N 2458/15; G01N 2333/4703; G01N 2560/00; G01N 2570/00; G01N 2333/765; G01N 2001/2893; G01N 2333/775; H01J 49/0009; Y10T 436/105831

See application file for complete search history.

(56) References Cited

U.S. PATENT DOCUMENTS

| 6,824,981 B2 | 11/2004 | Chait et al. |
| 2003/0045694 A1* | 3/2003 | Chait .................... C07K 1/047 |
| | | 536/23.1 |
| 2006/0183238 A1 | 8/2006 | Nimkar et al. |
| 2010/0178710 A1 | 7/2010 | Hamon et al. |
| 2011/0111513 A1 | 5/2011 | Baumann et al. |

FOREIGN PATENT DOCUMENTS

| EP | 1736480 A1 | 12/2006 |
| JP | 2000310617 | 11/2000 |
| WO | 95/04160 A2 | 2/1995 |
| WO | 97/27325 A2 | 7/1997 |
| WO | 97/27327 | 7/1997 |
| WO | 97/27331 | 7/1997 |
| WO | 98/26095 | 6/1998 |
| WO | 98/31830 | 7/1998 |
| WO | 200002895 A1 | 1/2000 |
| WO | 01/68664 A2 | 9/2001 |
| WO | 03/016861 A2 | 2/2003 |
| WO | 03/025576 A2 | 3/2003 |
| WO | 2004/031730 A2 | 4/2004 |
| WO | 2004/086050 A2 | 10/2004 |
| WO | 2005/114700 A2 | 12/2005 |

(Continued)

OTHER PUBLICATIONS

Product Bulletin iRAQ reagents. Amine-specific labeling reagents for multiplexed relative and absolute protein quantitation. Applied Biosystems 2004, Foster City, CA 94404, (Year: 2004).*
Gygi, S.P. et al., "Quantitative Analysis of Complex Protein Mixtures Using Isotope-Coded Affinity Tags", Nature Biotechnology, vol. 17, Oct. 1999, pp. 994-999.
Syka, J.E.P et al., "Peptide and protein sequence analysis by electron transfer dissociation mass spectrometry", PNAS, vol. 101, No. 26, Jun. 29, 2004, pp. 9528-9533.
Thompson, A. et al., "Tandem Mass Tags: A Novel Quantification Strategy for Comparative Analysis of Complex Protein Mixtures by MS/MS", Analytical Chemistry, vol. 75, No. 8, Apr. 15, 2003, pp. 1895-1904.

(Continued)

*Primary Examiner* — Shafiqul Haq
(74) *Attorney, Agent, or Firm* — Arent Fox LLP

(57) ABSTRACT

Provided is a method of assaying for an analyte, including combining a test sample having the analyte, with a calibration sample having at least two different aliquots of the analyte, each aliquot having a different known quantity of the analyte. The test sample and each aliquot are differentially labeled with one or more isobaric mass labels each with a mass spectrometrically distinct mass marker group, such that the test sample and each aliquot of the calibration sample can be distinguished by mass spectrometry. The method further includes determining by mass spectrometry the quantity of analyte in the test sample and in each aliquot, and calibrating the quantity of analyte in the test sample against known and determined quantities of analytes in the aliquots.

19 Claims, 12 Drawing Sheets

Specification includes a Sequence Listing.

(56) References Cited

FOREIGN PATENT DOCUMENTS

| WO | 2006/086540 A1 | 8/2006 |
|---|---|---|
| WO | 2007/012849 A2 | 2/2007 |

OTHER PUBLICATIONS

Ross, P.L. et al., "Multiplexed Protein Quantitation in *Saccharomyces cerevisiae* Using Amine-reactive Isobaric Tagging Reagents", Molecular & Cellular Proteomics 3.12, Methods in Clinical Proteomics Manuscripts, Sep. 22, 2004, M400129-MCP200, pp. 1154-1169.

Maskos, U. et al., "Oligonucleotide hybridisations on glass supports: a novel linker for oligonucleotide synthesis and hybridisation properties of oligonucleotides synthesised in situ", Nucleic Acids Research, vol. 20, No. 7, 1992, pp. 1679-1684.

Lloyd-Williams, P. et al., "Convergent Solid-Phase Peptide Synthesis", Tetrahedron, vol. 49, No. 48, 1993, pp. 11065-11133.

Geahlen, R.L. et al., "A General Method for Preparation of Peptides Biotinylated at the Carboxy Terminus", Analytical Biochemistry, vol. 202, 1992, pp. 68-70.

Sawutz, D.G. et al., "Synthesis and Molecular Characterization of a Biotinylated Analog of [Lys]Bradykinin", Peptides, vol. 12, 1991, pp. 1019-1024.

Natarajan, S. et al., "Site-Specific Biotinylation; a Novel Approach and its Application to Endothelin-1 Analogs and PTH-Analog", Int. J. Peptide Protein Res., vol. 40, 1992, pp. 567-574.

Bruegger, B. et al., "Quantitative analysis of biological membrane lipids at the low picomole level by nano-electrospray ionization tandem mass spectrometry", the National Academy of Sciences, Cell Biology, vol. 94, Mar. 1997, pp. 2339-2344.

Notice of Reasons for Rejection, JP 2009-553139, dispatched Nov. 13, 2012, pp. 1-4E.

Welti, R. et al., "Lipid species profiling: a high-throughput approach to identify lipid compositional changes and determine the function of genes involved in lipid metabolism and signaling", Current Opinion in Plant Biology, 2004, vol. 7, Issue 3, pp. 337-344.

International Search Report dated Oct. 22, 2008, 3 pages.

Dayon, L. et al., "Relative Quantification of Proteins in Human Cerebrospinal Fluids by MS/MS Using 6-plex Isobaric Tags", Analytical Chemistry, vol. 80, No. 8, Apr. 15, 2008, pp. 2921-2931.

* cited by examiner

MASS SPECTROMETRIC QUANTITATION

CROSS-REFERENCE TO RELATED APPLICATION(S)

This application is a continuation that claims priority to U.S. application Ser. No. 14/697,455 filed on Apr. 27, 2015, which is a continuation that claims priority to U.S. application Ser. No. 12/530,747 filed on Mar. 8, 2010, which is the U.S. national stage application of International Patent Application No. PCT/EP2008/052962 filed on Mar. 12, 2008, which claims priority to GB Application No. 0704764 filed on Mar. 12, 2007, the entire contents of each of which is incorporated herein by reference in their entireties.

FIELD OF THE INVENTION

This invention relates to mass spectrometry methods of assaying for an analyte by labelling test samples and calibration samples with isobaric mass labels. Relative and/or absolute quantitation of the analytes of interest is particularly facilitated by the invention.

BACKGROUND OF THE INVENTION

Various methods of labelling molecules of interest are known in the art, including radioactive atoms, fluorescent dyes, luminescent reagents, electron capture reagents and light absorbing dyes. Each of these labelling systems has features which make it suitable for certain applications and not others. For reasons of safety, interest in non-radioactive labelling systems lead to the widespread commercial development of fluorescent labelling schemes particularly for genetic analysis. Fluorescent labelling schemes permit the labelling of a relatively small number of molecules simultaneously, typically four labels can be used simultaneously and possibly up to eight. However the costs of the detection apparatus and the difficulties of analysing the resultant signals limit the number of labels that can be used simultaneously in a fluorescence detection scheme.

More recently there has been development in the area of mass spectrometry as a method of detecting labels that are cleavably attached to their associated molecule of interest. In many molecular biology applications one needs to be able to perform separations of the molecules of interest prior to analysis. These are generally liquid phase separations. Mass spectrometry in recent years has developed a number of interfaces for liquid phase separations which make mass spectrometry particularly effective as a detection system for these kinds of applications. Until recently Liquid Chromatography Mass Spectrometry was used to detect analyte ions or their fragment ions directly, however for many applications such as nucleic acid analysis, the structure of the analyte can be determined from indirect labelling. This is advantageous particularly with respect to the use of mass spectrometry because complex biomolecules such as DNA have complex mass spectra and are detected with relatively poor sensitivity. Indirect detection means that an associated label molecule can be used to identify the original analyte, where the label is designed for sensitive detection and a simple mass spectrum. Simple mass spectra mean that multiple labels can be used to analyse multiple analytes simultaneously.

PCT/GB98/00127 describes arrays of nucleic acid probes covalently attached to cleavable labels that are detectable by mass spectrometry which identify the sequence of the covalently linked nucleic acid probe. The labelled probes of this application have the structure Nu-L-M where Nu is a nucleic acid covalently linked to L, a cleavable linker, covalently linked to M, a mass label. Preferred cleavable linkers in this application cleave within the ion source of the mass spectrometer. Preferred mass labels are substituted poly-aryl ethers. This application discloses a variety of ionisation methods and analysis by quadrupole mass analysers, TOF analysers and magnetic sector instruments as specific methods of analysing mass labels by mass spectrometry.

PCT/GB94/01675 discloses ligands, and specifically nucleic acids, cleavably linked to mass tag molecules. Preferred cleavable linkers are photo-cleavable. This application discloses Matrix Assisted Laser Desorption Ionisation (MALDI) Time of Flight (TOF) mass spectrometry as a specific method of analysing mass labels by mass spectrometry.

PCT/US97/22639 discloses releasable non-volatile mass-label molecules. In preferred embodiments these labels comprise polymers, typically biopolymers which are cleavably attached to a reactive group or ligand, i.e. a probe. Preferred cleavable linkers appear to be chemically or enzymatically cleavable. This application discloses MALDI TOF mass spectrometry as a specific method of analysing mass labels by mass spectrometry.

PCT/US97/01070, PCT/US97/01046, and PCT/US97/01304 disclose ligands, and specifically nucleic acids, cleavably linked to mass tag molecules. Preferred cleavable linkers appear to be chemically or photo-cleavable. These applications disclose a variety of ionisation methods and analysis by quadrupole mass analysers, TOF analysers and magnetic sector instruments as specific methods of analysing mass labels by mass spectrometry.

None of these prior art applications mention the use of tandem or serial mass analysis for use in analysing mass labels.

Gygi et al. (Nature Biotechnology 17: 994-999, "Quantitative analysis of complex protein mixtures using isotope-coded affinity tags" 1999) disclose the use of 'isotope encoded affinity tags' for the capture of peptides from proteins, to allow protein expression analysis. In this article, the authors describe the use of a biotin linker, which is reactive to thiols, for the capture peptides with cysteine in them. A sample of protein from one source is reacted with the biotin linker and cleaved with an endopeptidase. The biotinylated cysteine-containing peptides can then be isolated on avidinated beads for subsequent analysis by mass spectrometry. Two samples can be compared quantitatively by labelling one sample with the biotin linker and labelling the second sample with a deuterated form of the biotin linker. Each peptide in the samples is then represented as a pair of peaks in the mass spectrum. Integration of the peaks in the mass spectrum corresponding to each tag indicates the relative expression levels of the peptide linked to the tags.

PCT/GB01/01122 discloses a set of two or more mass labels, each label in the set comprising a mass marker moiety attached via a cleavable linker to a mass normalisation moiety, the mass marker moiety being fragmentation resistant. The aggregate mass of each label in the set may be the same or different and the mass of the mass marker moiety of each label in the set may be the same or different. In any group of labels within the set having a mass marker moiety of a common mass each label has an aggregate mass different from all other labels in that group, and in any group of labels within the set having a common aggregate mass each label has a mass marker moiety having a mass different from that of all other mass marker moieties in that group, such that all of the mass labels in the set are distinguishable from each other by mass spectrometry. This application also discloses an array of mass labels, comprising two or more sets of mass labels as defined above. The aggregate mass of each of the mass labels in any one set is different from the aggregate mass of each of the mass labels in every other set in the array. This application further discloses methods of analysis comprising detecting an analyte by identifying by mass spectrometry a mass label or a combination of mass labels unique to the analyte. This application discloses a vast number of different specific mass labels. Preferred mass labels have the structure M-L-X, where M is the mass normalization group, L is the cleavable linker and X is the mass marker moiety. The nature of M and X is not particularly limited.

PCT/GB02/04240 discloses a set of two or more mass labels, each label in the set comprising a mass marker moiety attached via at least one amide bond to a mass normalisation moiety. The mass marker moiety comprises an amino acid and the mass normalisation moiety comprises an amino acid. As for PCT/GB01/01122 the aggregate mass of each label in the set may be the same or different and the mass of the mass marker moiety of each label in the set may be the same or different such that all of the mass labels in the set are distinguishable from each other by mass spectrometry. As for PCT/GB01/01122 this application also discloses an array of mass labels and a method of analysis. This application is specifically directed to the analysis of peptides and mass labels with mass normalisation moieties and mass marker moieties comprising at least one amino acid.

Whilst the mass labels and methods of analysis disclosed in PCT/GB01/01122 and PCT/GB02/04240 are by and large successful, there is still a requirement to provide improved reagents and methods of relatively or absolutely quantifying an analyte by providing a mass labelled reference corresponding to the said analyte, which labelled reference material can be added to the sample containing the analyte and wherein the analyte and the reference material can be simultaneously quantified and identified by tandem mass spectrometry.

The development of isobaric mass tags in the late 1990's has revolutionised biomarker discovery. The ability to analyse multiple samples in theoretically unlimited numbers in a single LC-MS/MS workflow increases throughput whilst at the same time reducing analytical variability. Whilst application of these methodologies provides enhanced biomarker discovery there remains a significant bottleneck in biomarker validation and development of routine assays capable of analysing large numbers of samples. This bottleneck is created by the need to obtain high specificity reagents, typically in the form of antibodies, against each candidate biomarker. The production of antibodies is laborious, costly and takes several months with no guarantee of success.

In addition to cost and time constraints, use of antibody based methods for biomarker validation are also hampered by the limit of such methods to detect analytes with widely different normal and regulated concentration ranges. For example it is seldom possible to measure more than 10 up to 20 different analytes in a single multiplex assay using antibody arrays. Where the normal concentration of such proteins is separated by more than one log (i.e. micromolar to nanomolar) it is even less likely that such multiplex antibody arrays can accurately quantify each analyte and multiplexing rates are consequently significantly lower.

There remains therefore a need for improved methods of quantitatively detecting and routinely measuring analytes by mass spectrometry in a wide range of samples.

The majority of protein biomarker discovery is performed using mass spectrometry linked to various methods of protein separation. More recently a number of groups have proposed using mass spectrometers to provide absolute quantitation of proteins based on one or more isotopically labelled reference peptides. WO 03/016861 discloses one such embodiment termed 'AQUA' which uses synthetic peptides incorporating one or more stable isotope labelled amino acids as a reference standard. Such peptides are normally selected based on a number of criteria including their ionisation behaviour, physicochemical properties, and ease and cost of manufacture. In an Aqua experiment the reference peptides are spiked into the sample of interest at a defined concentration. Because they are labelled with stable isotopes the reference peptide will produce a distinct peak from the naturally occurring form of the peptide in the sample of interest. Typically the AQUA peptide mass will be separated by an increased mass of about 5-50 daltons compared to the natural peptide. By comparing the relative peak intensities of the natural peptide and its AQUA equivalent the absolute concentration of the parent peptide in the sample can be determined.

Whilst AQUA is able to measure absolute quantities of multiple proteins in a single experiment, it is not suitable for development of reference standard curves to cover a range of naturally occurring concentrations. For biomarker validation studies this may be problematic since regulation of protein expression may result in a ten-fold or greater range of concentrations for a given protein. Using a single reference standard may lead to inaccurate quantitation of natural peptide levels at the extremes of regulation and it would be desirable to provide a means of including readily distinguishable reference peptides at several different concentrations to cover the physiological range and which provide an appropriate standard curve against which the level of the target peptide in a sample can be read. Producing such curves using AQUA would be difficult since each added peptide increases the complexity of the MS profile. In addition, to ensure that the standard curve is built only on the reference peptides it would be advisable if not essential to perform sequence confirmation by MS/MS of each reference peptide as well as for the target peptide in the sample.

SUMMARY OF THE INVENTION

It is an aim of the present invention to solve one or more of the problems with the prior art described above. Specifically, it is an aim or the present invention to provide an improved mass spectrometric method of assaying for an analyte.

To overcome the limitations of the art the inventors have developed a method of quantifying molecules of interest using isobarically tagged reference biomolecules or complex biological materials, for example peptides, that allow construction of multi-point standard curves for each analyte without increasing MS complexity.

Accordingly, the present invention provides a method of assaying for an analyte, which method comprises:
a) combining a test sample, which may comprise the analyte, with a calibration sample comprising at least two different aliquots of the analyte, each aliquot having a different known quantity of the analyte, wherein the sample and each aliquot are differentially labelled with one or more isobaric mass labels each with a mass spectrometrically distinct mass marker group, such that the test sample and each aliquot of the calibration sample can be distinguished by mass spectrometry;
b) determining by mass spectrometry the quantity of the analyte in the test sample and the quantity of analyte in each aliquot in the calibration sample, and calibrating the quantity of the analyte in the test sample against the known and determined quantities of the analytes in the aliquots in the calibration sample.

The different aliquots each have a known quantity of the analyte. The term "known quantity" means that the absolute quantity, or a qualitative quantity of the analyte in each aliquot of the calibration sample is known. A qualitative quantity in the present context means a quantity which is not known absolutely, but may be a range of quantities that are expected in a subject having a particular state, for example a subject in a healthy or diseased state, or some other expected range depending on the type of test sample under investigation. Each aliquot is "different" since it contains a different quantity of the analyte. Typically this is achieved by taking different volumes from a standard sample, especially for qualitative quantities where taking different volumes will ensure that different quantities are present in each aliquot in a desired ratio, without needing to know the absolute quantities.

Preferably, step (b) comprises:
i) in a mass spectrometer selecting and fragmenting ions of a mass to charge ratio corresponding to the analyte labelled with the mass label, detecting and producing a mass spectrum of fragment ions, and identifying the fragment ions corresponding to the mass marker groups of the mass labels;
ii) determining the quantity of the analyte in each test sample on the basis of the quantity of their mass marker groups in a mass spectrum relative to the quantities of the mass marker groups from the aliquots of the calibration sample in the same mass spectrum.

Typically, the fragmentation is caused by Collision Induced Dissociation (CID), Surface Induced Dissociation (SID), Electron Capture Dissociation (ECD), Electron Tranfer Dissociation (ETD), or Fast Atom Bombardment.

Electron capture dissociation (ECD) is a method of fragmenting multiply charged (protonated) peptide or proteins ions for tandem mass spectrometric analysis (structural elucidation). In this method multiply protonated peptide or proteins are confined in the Penning trap of a Fourier transform ion cyclotron resonance (FTICR) mass spectrometer and exposed to electrons with near-thermal energies. The capture of a thermal electron by a protonated peptide is exothermic ($\approx 6$ eV; 1 eV=$1.602 \times 10^{-19}$ J), and causes the peptide backbone to fragment by a nonergodic process (i.e., a process that does not involve intramolecular vibrational energy redistribution).

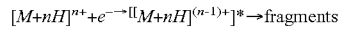

In addition, one or more protein cations can be neutralized with low energy electrons to cause specific cleavage of bonds to form c, z products, in contrast to b, y products formed by other techniques such as collisionally activated dissociation (CAD; also known as collision-induced dissociation, CID). Since thermal electrons introduced into the RF fields of RF 3D quadrupole ion trap (QIT), quadrupole time-of-flight, or RF linear 2D quadrupole ion trap (QLT) instruments maintain their thermal energy only for a fraction of a microsecond and are not trapped in these devices, ECD remains a technique exclusively used with FTICR, the most expensive type of MS instrumentation.

Electron transfer dissociation (ETD) is a method of fragmenting multiply protonated peptide or proteins ions for tandem mass spectrometric analysis (structural elucidation). Similar to electron capture dissociation (ECD), ETD induces fragmentation of cations (e.g. multiple charged peptide or proteins) by transferring electrons to them. In contrast to ECD, ETD does not use free electrons but employs radical anions for this purpose (e.g. anthracene or azobenzene anions which possess sufficiently low electron affinities to act as electron donors).

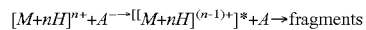

After the electron transfer, ETD results in a similar fragmentation pattern as ECD, i.e. the formation of so called c and z ions. Based on the different way of electron transfer, ETD can be implemented on various "lower cost" mass spectrometers like quadrupole ion trap (QIT) or RF linear 2D quadrupole ion trap (QLT) instruments which are not appropriate for ECD.

For an appropriate reference see John E. P. Syka, Joshua J. Coon, Melanie J. Schroeder, Jeffrey Shabanowitz, and Donald F. Hunt, PNAS, Vol. 101, no. 26, pp. 9528-9533.

The most preferred embodiment is where the fragmentation is caused by collision-induced dissociation. Collision-induced dissociation occurs during an MS/MS experiment. The term 'MS/MS' in the context of mass spectrometry refers to an experiment which involves selecting ions, subjecting selected ions to CID and subjecting the fragment ions to further analysis.

This method enables multi-point calibration of the quantity of each analyte without increasing MS complexity. Analyte quantitation is obtained in the MS/MS profile, and the analyte in the sample and in the calibration sample can be simultaneously quantified and identified by tandem mass spectrometry. This method provides means for the measurement of up to 10, up to 20, up to 50 or more analytes in a single LC-MS/MS experiment.

The method may comprise a further step prior to step (a) of differentially labelling each test sample or each aliquot of the calibration sample with one or more isobaric mass labels. In a preferred embodiment the method also comprises a further step of combining the differentially labelled aliquots to produce a calibration sample prior to step (a).

The test sample may comprise a plurality of different analytes, and in this case a calibration sample is provided for each different analyte, and step (b) is repeated for each different analyte. In one embodiment the plurality of analytes are peptide fragments of a protein or polypeptide which are produced by chemical or enzymatic processing of the protein or polypeptide prior to step (a). In a particular embodiment, the plurality of analytes are peptides from the same protein or polypeptide.

In one embodiment, a plurality of test samples is assayed for an analyte. In a particular embodiment, each of the plurality of test samples is assayed for the same analyte. In this case, each of the test samples may be differentially labelled with one or more isobaric mass labels and combined with a single calibration sample in step (a), and the quantity of the analyte in each sample is determined simultaneously in step (b). In another embodiment, each test sample is labelled with the same mass label, and steps (a) and (b) are repeated for each different sample. The same calibration sample can be used for each test sample to be assayed. Typically, the same known volume of the calibration sample comprising at least two aliquots of the analyte is added to each different test sample. This method is particularly useful in clinical studies involving multiple samples from patients.

If a large quantity of the calibration sample is prepared and fractions taken, the same calibration sample can be used by multiple laboratories, facilitating cross-study and cross-laboratory comparisons.

In a method according to the invention, the quantity of analyte in each aliquot in the calibration sample is a known absolute quantity. This allows for the absolute quantity of an analyte in a test sample to be determined in step (b).

In an alternative method, the absolute quantity of an analyte in each aliquot in the calibration sample is not known. In this embodiment, the quantity of analyte in each aliquot in the calibration sample is a known qualitative quantity. The calibrating step comprises calibrating the quantity of the analyte in the test sample against the qualitative and determined quantities of the analytes in the aliquots of the calibration sample. In a particular embodiment, the qualitative quantity is an expected range of quantities of analyte in a subject having a particular state, such as a healthy or diseased state.

In a preferred embodiment, the quantity of analyte in each different aliquot is selected to reflect the known or suspected variation in the quantity of the analyte in the test sample. In a yet further preferred embodiment, aliquots are provided which correspond to the upper and lower limits, and optionally intermediate points within a range of the known or suspected quantities of the analyte found in test samples of healthy or diseased subjects. The different quantities of analyte present in the different aliquots may correspond to the known or suspected quantity of analyte present in a test sample which has been incubated for different periods of time.

The calibration sample may comprise an analyte in a quantity that indicates the presence and/or stage of a particular disease. The calibration sample may also comprise the analyte in a quantity which indicates the efficacy and/or toxicity of a therapy.

The method according to the present invention may comprise a further step of separating the components of the samples prior to step (a). The method may also comprise a step of digesting each sample with at least one enzyme to digest components of the samples prior to step (a). In one embodiment the samples are labelled with the isobaric mass labels prior to digestion. In another embodiment, the labelling step occurs after the digestion step. The enzyme digestion step may also occur after step (a) but before step (b).

In another embodiment, the mass labels used in the method further comprise an affinity capture ligand. The affinity capture ligand of the mass label binds to a counter-ligand so as to separate the isobarically labeled analytes from the unlabelled analytes after step (a) but before step (b). The affinity capture ligand provides a means of enrichment of the analytes of interest, thereby increasing analytical sensitivity.

The method according to the invention may further include the step of separating the isobarically labeled analytes electrophoretically or chromatographically after step (a) but before step (b).

Although the structure of the mass labels used in the present invention is not especially limited, providing that they are isobaric and have mass spectrometrically distinct mass marker groups (moieties), in preferred embodiments the mass label comprises the following structure:

X-L-M wherein X is a mass marker moiety, L is a cleavable linker and M is a mass normalisation moiety. L may be a single bond, or part of X, or part of M. These mass labels may be attached at any point to the analyte in the test or calibration samples, e.g. through M, L or X. Preferably, they are attached through M, e.g. the label would comprise the structure:

(X-L-M)-

This is typically effected by including a reactive functionality in the mass label to allow it to bind to the analyte, e.g:

X-L-M-reactive functionality

When the labels comprise a reactive functionality these are termed reactive mass labels.

In preferred embodiments, X is a mass marker moiety comprising the following group:

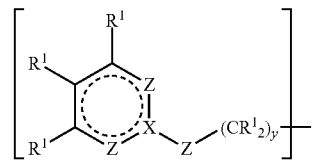

wherein the cyclic unit is aromatic or aliphatic and comprises from 0-3 double bonds independently between any two adjacent atoms; each Z is independently N, N($R^1$), C($R^1$), CO, CO($R^1$) (i.e. —O—C($R^1$)— or —C($R^1$)—O—), C($R^1$)$_2$, O or S; $X^1$ is N, C or C($R^1$); each $R^1$ is independently H, a substituted or unsubstituted straight or branched $C_1$-$C_6$ alkyl group, a substituted or unsubstituted aliphatic cyclic group, a substituted or unsubstituted aromatic group or a substituted or unsubstituted heterocyclic group; and y is an integer from 0-10.

The reactive functionality for attaching the mass label to the analyte is not especially limited and may comprise any appropriate reactive group.

The term mass label used in the present context is intended to refer to a moiety suitable to label an analyte for determination. The term label is synonymous with the term tag.

The term mass marker moiety used in the present context is intended to refer to a moiety that is to be detected by mass spectrometry. The term mass marker moiety is synonymous with the term mass marker group or the term reporter group.

The term mass normalisation moiety used in the present context is intended to refer to a moiety that is not necessarily to be detected by mass spectrometry, but is present to ensure that a mass label has a desired aggregate mass. The mass normalisation moiety is not particularly limited structurally, but merely serves to vary the overall mass of the mass label.

In the above general formula, when Z is C($R^1$)$_2$, each $R^1$ on the carbon atom may be the same or different (i.e. each $R^1$ is independent). Thus the C($R^1$)$_2$ group includes groups such as CH($R^1$), wherein one $R^1$ is H and the other $R^1$ is another group selected from the above definition of $R^1$.

In the above general formula, the bond between $X^1$ and the non-cyclic Z may be single bond or a double bond depending upon the selected $X^1$ and Z groups in this position. For example, when $X^1$ is N or C($R^1$) the bond from $X^1$ to the non-cyclic Z must be a single bond. When $X^1$ is C, the bond from $X^1$ to the non-cyclic Z may be a single bond or a double bond depending upon the selected non-cyclic Z group and cyclic Z groups. When the non-cyclic Z group is N or C($R^1$) the bond from non-cyclic Z to $X^1$ is a single bond or if y is 0 may be a double bond depending on the selected $X^1$ group and the group to which the non-cyclic Z is attached. When the non-cyclic Z is $N(R^1)$, $CO(R^1)$, CO, $C(R^1)_2$, O or S the bond to $X^1$ must be a single bond. The person skilled in the art may easily select suitable $X^1$, Z and $(CR^1{}_2)_y$ groups with the correct valencies (single or double bond links) according to the above formula.

The present inventors have discovered that the mass labels defined above can be easily identified in a mass spectrometer and also allow sensitive quantification.

In a preferred embodiment the aggregate molecular weight of the mass label is 600 Daltons or less, more preferably 500 Daltons or less, still more preferably 400 Daltons or less, most preferably from 300 to 400 Daltons. Particularly preferred molecular weights of the mass labels are 324, 338, 339 and 380 Daltons. These preferred embodiments are particularly advantageous because the small size of the mass labels means that the size of the peptide to be detected is minimally increased when labelled with the mass label. Therefore, the peptide labelled with the mass label may be viewed in the same mass spectrum window as unlabelled peptide when analysed by mass spectroscopy. This facilitates identification of peaks from the mass label itself.

In a preferred embodiment, the molecular weight of the mass marker moiety is 300 Daltons or less, preferably 250 Daltons or less, more preferably 100 to 250 Daltons, most preferably 100-200 Daltons. These preferred embodiments are particularly advantageous because the small size of the mass marker moiety means that it produces a peak in the silent region of a mass spectrum, which allows the mass marker to be easily identified from the mass spectrum and also allows sensitive quantification.

The term silent region of a mass spectrum (such as an MS/MS spectrum) used in the present context is intended to refer to the region of a mass spectrum with low background "noise" caused by peaks relating to the presence of fragments generated by fragmentation of the labelled peptides. An MS/MS spectrum is obtained by the fragmentation of one peak in MS-mode, such that no contaminants, such as buffering reagents, denaturants and detergent should appear in the MS/MS spectrum. In this way, quantification in MS/MS mode is advantageous. Thus, the term silent region is intended to refer to the region of the mass spectrum with low "noise" caused by peaks relating to the peptide to be detected. For a peptide or protein, the silent region of the mass spectrum is less than 200 Daltons.

The present inventors have also discovered that the reactive mass labels defined above are easily and quickly reacted with a protein to form a labelled protein.

In the present invention a set of two or more mass labels is employed. The labels in the sets are isobaric mass labels each having a mass marker of a different mass. Thus, each label in the set is as defined above and wherein each mass normalisation moiety ensures that a mass label has a desired aggregate mass, and wherein the set comprises:
mass labels having a mass marker moiety, each mass marker moiety having a mass different from that of all other mass marker moieties in the set, and each label in the set having a common aggregate mass; and wherein all the mass labels in the set are distinguishable from each other by mass spectroscopy.

The term "isobaric" means that the mass labels have substantially the same aggregate mass as determined by mass spectrometry. Typically, the average molecular masses of the isobaric mass labels will fall within a range of ±0.5 Da of each other. The term "labels" shall be synonymous with the term "tags". In the context of the present invention, the skilled addressee will understand that the term "mass marker moiety" and the term "reporter group" can be used interchangeably.

The number of labels in the set is not especially limited, provided that the set comprises a plurality of labels. However, it is preferred if the set comprises two or more, three or more, four or more, or five or more labels, more preferably six or more labels, most preferably eight or more labels.

The term aggregate mass in the present context refers to the total mass of the mass label, i.e. the sum of the masses of the mass marker moiety, the cleavable linker, the mass normalisation moiety and any other components of the mass label.

The mass of the mass normalisation moiety will be different in each mass label in the set. The mass of the mass normalisation moiety in each individual mass label will be equal to the common aggregate mass minus the mass of the particular mass marker moiety in that mass label and minus the mass of the cleavable linker.

All mass labels in the set are distinguishable from each other by mass spectroscopy. Therefore, a mass spectrometer can discriminate between the mass labels, i.e. the peaks derived from individual mass labels can be clearly separated from one another. The difference in mass between the mass marker moieties means that a mass spectrometer can discriminate between ions derived from different mass labels or mass marker moieties.

The present invention may also employ an array of mass labels, comprising two or more sets of mass labels as defined above, wherein the aggregate mass of each of the mass labels in any one set is different from the aggregate mass of each of the mass labels in every other set in the array.

In preferred embodiments of the invention, the array of mass labels are preferably all chemically identical (substantially chemically identical). The term "substantially chemically identical" means that the mass labels have the same chemical structure, into which particular isotopic substitutions may be introduced or to which particular substituents may be attached.

In further preferred embodiments of this invention, the mass labels may comprise a sensitivity enhancing group. The mass labels are preferably of the form:

sensitivity enhancing group -X-L-M- reactive functionality

In this example the sensitivity enhancing group is usually attached to the mass marker moiety, since it is intended to increase the sensitivity of the detection of this moiety in the mass spectrometer. The reactive functionality is shown as being present and attached to a different moiety than the sensitivity enhancing group. However, the mass labels need not be limited in this way and in some cases the sensitivity enhancing group may be attached to the same moiety as the reactive functionality.

In a further aspect, the present invention provides a method of assaying a low abundance analyte in a sample, which method comprises the method of mass spectrometric analysis as defined above, wherein the calibration sample comprises a large quantity of the analyte to be assayed, and the sample may comprise the analyte in low abundance. In this method, the analyte is present in the calibration sample in a quantity such that it can be readily detected and separated together with the analyte in the sample by a method such as one or two-dimensional gel electrophoresis, free-flow electrophoresis, capillary electrophoresis, off-gel isoelectric focusing or liquid chromatography mass spectrometry prior to step (b). Preferably, the analyte in the sample is a protein, and the analyte in the calibration sample is a recombinant form of the protein in the sample.

BRIEF DESCRIPTION OF THE DRAWINGS

The present invention will now be described further by way of example only with reference to the accompanying drawings, in which.

DETAILED DESCRIPTION OF THE INVENTION

Figure 1:
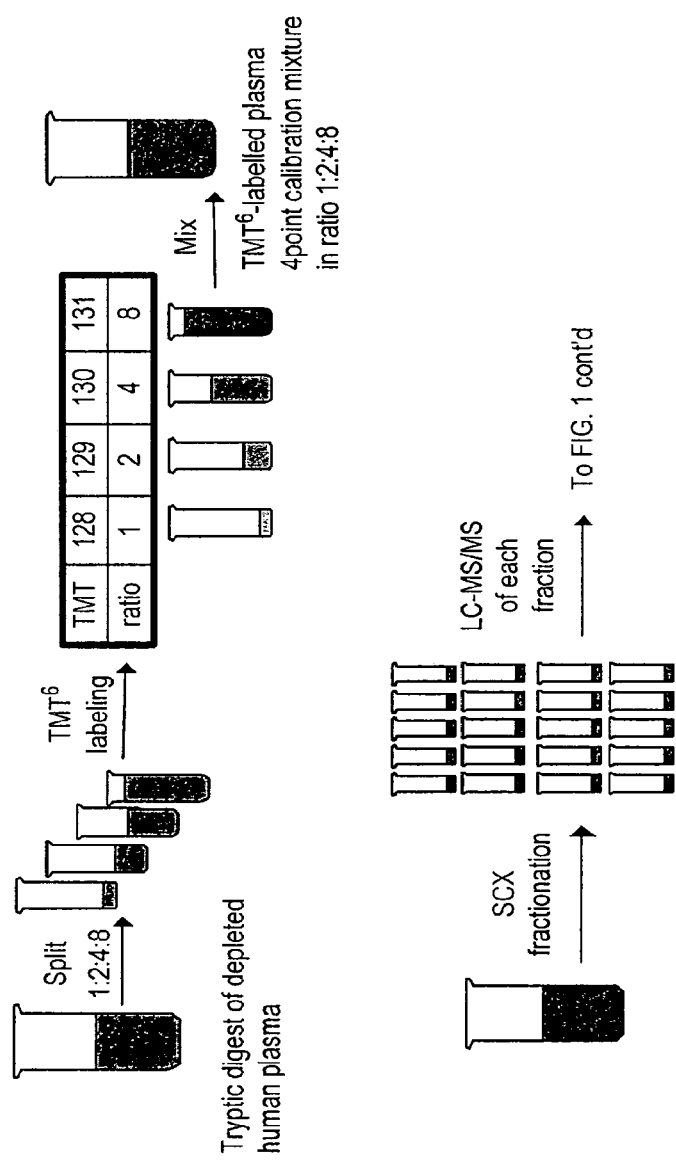
FIG. 1 shows a schematic of a method according to the present invention.
Figure 1:
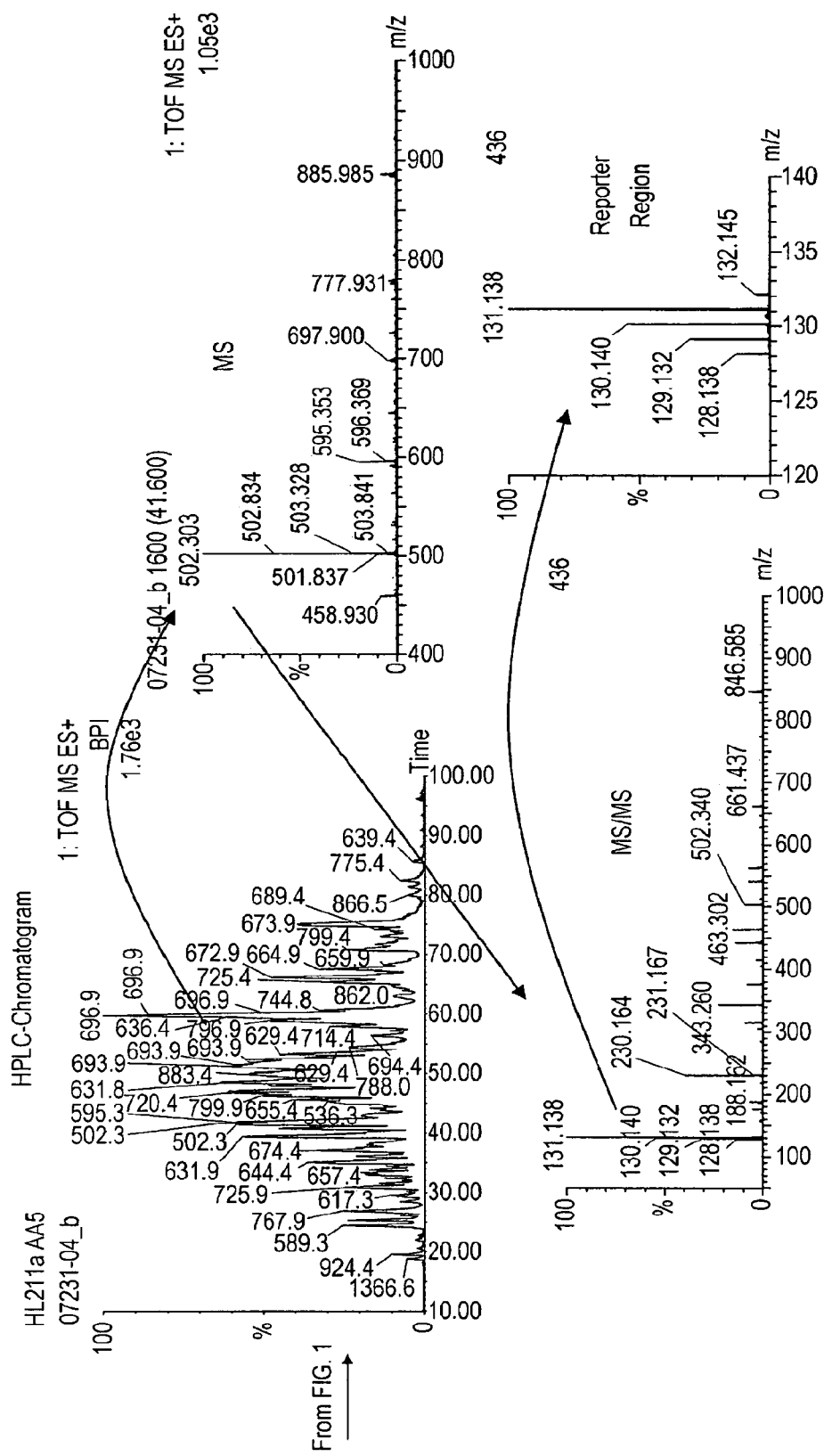

The present invention will now be described in detail.

This invention provides useful reagents for determining relative and/or absolute quantities of analytes such as peptides, proteins, nucleotides and nucleic acids and means of their production. Specifically this invention relates to isobarically labelled analytes and/or calibration samples for detection by tandem mass spectrometry and associated methods of analysing test samples into which such calibration samples have been added. Relative and/or absolute quantitation of the analytes is particularly facilitated by the invention.

This invention provides new methods for assaying analytes by mass spectrometry in a variety of settings including measurement of protein, lipid, carbohydrate and nucleic acid changes in cells, tissues and fluids in human, veterinary, plant, microbial, pharmaceutical, environmental and security sciences.

In the methods according to the present invention the quantity of the analyte in the test sample and in each aliquot of the calibration sample is determined by mass spectrometry. A calibration function is used to relate the quantity of the analyte in the test sample as measured by mass spectrometry to the actual quantity of the analyte in the test sample. This calibration function uses the quantities of the analyte in each aliquot of the calibration sample (both the actual quantities in the aliquots prior to analysis and the corresponding quantities as measured by mass spectrometry) as variables.

In a preferred embodiment, the method comprises a step of plotting a graph of the quantity of the analyte in each aliquot versus the quantity of the analyte in each aliquot as determined by mass spectrometry. This step may instead simply involve calculation. The quantity of the analyte in the sample is then calculated by measuring the quantity in the sample as determined by mass spectrometry against the calibration graph. In the context of this invention, a reference to "a quantity as measured by mass spectrometry" is typically an ion abundance, ion intensity, or other signal measured by mass spectrometry which relates to the quantity of an analyte.

Typically, the method comprises:
  i) in a mass spectrometer selecting and fragmenting ions of a mass to charge ratio corresponding to the analyte labelled with the mass label, detecting and producing a mass spectrum of fragment ions, and identifying the fragment ions corresponding to the mass marker groups of the mass labels;
  ii) determining the quantity of the analyte in each test sample on the basis of the quantity of their mass marker groups in a mass spectrum relative to the quantities of the mass marker groups from the aliquots of the calibration sample in the same mass spectrum.

In a particular embodiment, the method comprises the steps of:
  1. Optionally preparing the isobarically labelled reference material containing a reference biomolecule or mixture of reference biomolecules by reacting with a set of mass labels according to this invention;
  2. Labelling a sample in which the quantity of the biomolecule or mixture of biomolecules is to be quantified by reacting with one of the same set of mass labels as used in step 1 above according to this invention;
  3. Adding a known amount of the isobarically labelled reference material into the isobarically labelled test sample prepared in step 2;
  4. Optionally separating the isobarically labelled biomolecules electrophoretically or chromatographically;
  5. Ionising the labelled biomolecules in a mass spectrometer;
  6. Selecting ions of a predetermined mass to charge ratio corresponding to the mass to charge ratio of the preferred ions of the labelled biomolecule in a mass analyser;
  7. Inducing dissociation of these selected ions by collision or electron transfer;
  8. Detecting the collision products to identify collision product ions that are indicative of the mass labels;
  9. Producing a standard curve of ion intensity versus biomolecule amount based on intensity of the collision product ions that are indicative of the mass labels;

10. Calculating the absolute or relative abundance of the biomolecule or mixture of biomolecules.

In relation to this invention the term "mass spectrometry" shall include any type of mass spectrometry capable of fragmentation analysis. The mass spectrometers suitable for use in the present invention include instruments that comprise any form of MS/MS analyser such as a triple quadropole mass spectrometer equipped with a collision chamber, an ion trap mass spectrometer capable of fragmenting selected precursor ions by fast atom bombardment, collision induced dissociation, electron transfer dissociation or any other form of parent ion fragmentation, and matrix assisted laser desorption/ionisation (MALDI) mass spectrometers fitted with a dual time of flight (TOF/TOF) analyser and a means of parent ion fragmentation.

In certain embodiments the step of selecting the ions of a predetermined mass to charge ratio is performed in the first mass analyser of a serial instrument. The selected ions are then channelled into a separate collision cell where they are collided with a gas or a solid surface. The collision products are then channelled into a further mass analyser of a serial instrument to detect collision products. Typical serial instruments include triple quadrupole mass spectrometers, tandem sector instruments and quadrupole time of flight mass spectrometers.

In other embodiments, the step of selecting the ions of a predetermined mass to charge ratio, the step of colliding the selected ions with a gas and the step of detecting the collision products are performed in the same zone of the mass spectrometer. This may be effected in ion trap mass analysers and Fourier Transform Ion Cyclotron Resonance mass spectrometers, for example.

In the present invention, matrix assisted laser desorption/ionisation (MALDI) techniques may be employed. MALDI requires that the biomolecule solution be embedded in a large molar excess of a photo-excitable 'matrix'. The application of laser light of the appropriate frequency results in the excitation of the matrix which in turn leads to rapid evaporation of the matrix along with its entrapped biomolecule. Proton transfer from the acidic matrix to the biomolecule gives rise to protonated forms of the biomolecule which can be detected by positive ion mass spectrometry, particularly by Time-Of-Flight (TOF) mass spectrometry. Negative ion mass spectrometry is also possible by MALDI TOF. This technique imparts a significant quantity of translational energy to ions, but tends not to induce excessive fragmentation despite this. The laser energy and the timing of the application of the potential difference used to accelerate the ions from the source can be used to control fragmentation with this technique. This technique is highly favoured due to its large mass range, due to the prevalence of singly charged ions in its spectra and due to the ability to analyse multiple peptides simultaneously. The TOF/TOF technique may be employed in the present invention.

The photo-excitable matrix comprises a 'dye', i.e. a compound that strongly absorbs light of a particular frequency, and which preferably does not radiate that energy by fluorescence or phosphorescence but rather dissipates the energy thermally, i.e. through vibrational modes. It is the vibration of the matrix caused by laser excitation that results in rapid sublimation of the dye, which simultaneously takes the embedded analyte into the gas phase.

Although MALDI techniques are useful in the context of the present invention, the invention is not limited to this type of technique, and other techniques common to the art can be employed by the skilled person in the present invention, if desired. For example electrospray or nanoelectrospray mass spectrometry may be employed.

The term "analyte" is not particularly limiting, and the methods according to the present invention may be employed to assay any type of molecule provided that it can be analysed by mass spectrometry, and is capable of being labelled by an isobaric mass label with a mass spectrometrically distinct mass marker group. Analytes include amino acids, peptides, polypeptides, proteins, glycoproteins, lipoproteins, nucleic acids, polynucleotides, oligonucleotides, DNA, RNA, peptide-nucleic acids, sugars, starches and complex carbohydrates, fats and complex lipids, polymers and small organic molecules such as drugs and drug-like molecules. Preferably the analyte is a peptide, protein, nucleotide or nucleic acid.

In relation to this invention the term protein shall encompass any molecule comprising two or more amino acids including di-peptides, tri-peptides, peptides, polypeptides and proteins.

In relation to this invention the term nucleic acid shall encompass any molecule comprising two or more nucleotide bases including di-nucleotides, tri-nucleotides, oligonucleotides, deoxyribonucleic acids, ribonucleic acids and peptide nucleic acids.

In relation to this invention the term analyte shall be synonymous with the term biomolecule.

The mass labels employed to tag the analytes in the present invention will now be described in more detail.

The skilled artisan will understand that the nature of the isobaric mass label is not particularly limiting. Various suitable isobaric mass labels are known in the art such as Tandem Mass Tags (Thompson et al., 2003, Anal. Chem. 75(8): 1895-1904 (incorporated herein by reference) disclosed in WO 01/68664 (incorporated herein by reference) and WO 03/025576 (incorporated herein by reference), iPROT tags disclosed in U.S. Pat. No. 6,824,981 (incorporated herein by reference) and iTRAQ tags (Pappin et al., 2004, Methods in Clinical Proteomics Manuscript M400129-MCP200 (incorporated herein by reference)). Any of these isobaric mass labels are suitable for preparation of the samples and calibration samples and performing the methods of the current invention.

Mass Marker Moiety

In a preferred embodiment, the present invention uses a mass label as defined above wherein the molecular weight of the mass marker moiety is 300 Daltons or less, preferably 250 Daltons or less, more preferably 100 to 250 Daltons, most preferably 100-200 Daltons. Particularly preferred molecular weights of the mass marker moiety are 125, 126, 153 and 154 Daltons, or weights in which one or more or all of the 12 C atoms are replaced by 13 C atoms, e.g. for a non-substituted mass marker moiety having a weight of 125, masses for its substituted counterparts would be 126, 127, 128, 129, 130 and 131 Daltons for substitution with 1, 2, 3, 4, 5 and 6 13 C atoms respectively and/or one or more or all of the 14N atoms are replaced by 15N atoms.

The components of the mass marker moiety of this invention are preferably fragmentation resistant so that the site of fragmentation of the markers can be controlled by the introduction of a linkage that is easily broken by Collision Induced Dissociation (CID), Surface Induced Dissociation, Electron Capture Dissociation (ECD), Electron Tranfer Dissociation (ETD), or Fast Atom Bombardment. In the most preferred embodiment, the linkage is easily broken by CID.

The mass marker moiety used in the present invention typically comprises the following group:

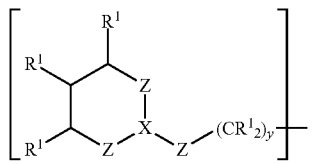

wherein the cyclic unit is aromatic or aliphatic and comprises from 0-3 double bonds independently between any two adjacent atoms; each Z is independently N, N(R$^1$), C(R$^1$), CO, CO(R$^1$) (i.e. —O—C(R1)- or —C(R1)-O—), C(R$^1$)$_2$, O or S; X is N, C or C(R$^1$); each R$^1$ is independently H, a substituted or unsubstituted straight or branched C$_1$-C$_6$ alkyl group, a substituted or unsubstituted aliphatic cyclic group, a substituted or unsubstituted aromatic group or a substituted or unsubstituted heterocyclic group; and y is an integer from 0-10.

The substituents of the mass marker moiety are not particularly limited and may comprise any organic group and/or one or more atoms from any of groups IIIA, IVA, VA, VIA or VIIA of the Periodic Table, such as a B, Si, N, P, O, or S atom or a halogen atom (e.g. F, Cl, Br or I).

When the substituent comprises an organic group, the organic group preferably comprises a hydrocarbon group. The hydrocarbon group may comprise a straight chain, a branched chain or a cyclic group. Independently, the hydrocarbon group may comprise an aliphatic or an aromatic group. Also independently, the hydrocarbon group may comprise a saturated or unsaturated group.

When the hydrocarbon comprises an unsaturated group, it may comprise one or more alkene functionalities and/or one or more alkyne functionalities. When the hydrocarbon comprises a straight or branched chain group, it may comprise one or more primary, secondary and/or tertiary alkyl groups. When the hydrocarbon comprises a cyclic group it may comprise an aromatic ring, an aliphatic ring, a heterocyclic group, and/or fused ring derivatives of these groups. The cyclic group may thus comprise a benzene, naphthalene, anthracene, indene, fluorene, pyridine, quinoline, thiophene, benzothiophene, furan, benzofuran, pyrrole, indole, imidazole, thiazole, and/or an oxazole group, as well as regioisomers of the above groups.

The number of carbon atoms in the hydrocarbon group is not especially limited, but preferably the hydrocarbon group comprises from 1-40 C atoms. The hydrocarbon group may thus be a lower hydrocarbon (1-6 C atoms) or a higher hydrocarbon (7 C atoms or more, e.g. 7-40 C atoms). The number of atoms in the ring of the cyclic group is not especially limited, but preferably the ring of the cyclic group comprises from 3-10 atoms, such as 3, 4, 5, 6 or 7 atoms.

The groups comprising heteroatoms described above, as well as any of the other groups defined above, may comprise one or more heteroatoms from any of groups IIIA, IVA, VA, VIA or VIIA of the Periodic Table, such as a B, Si, N, P, O, or S atom or a halogen atom (e.g. F, Cl, Br or I). Thus the substituent may comprise one or more of any of the common functional groups in organic chemistry, such as hydroxy groups, carboxylic acid groups, ester groups, ether groups, aldehyde groups, ketone groups, amine groups, amide groups, imine groups, thiol groups, thioether groups, sulphate groups, sulphonic acid groups, and phosphate groups etc. The substituent may also comprise derivatives of these groups, such as carboxylic acid anhydrides and carboxylic acid halides.

In addition, any substituent may comprise a combination of two or more of the substituents and/or functional groups defined above.

The cleavable linker of the mass label used in the present invention is not especially limited. Preferably, the cleavable linker is a linker cleavable by Collision Induced Dissociation, Surface Induced Dissociation, Electron Capture Dissociation (ECD), Electron Transfer Dissociation (ETD), or Fast Atom Bombardment. In the most preferred embodiment, the linkage is cleavable by CID. The linker may comprise an amide bond.

Linker

In the discussion above and below reference is made to linker groups which may be used to connect molecules of interest to the mass label compounds used in this invention. A variety of linkers is known in the art which may be introduced between the mass labels of this invention and their covalently attached biological molecule. Some of these linkers may be cleavable. Oligo- or poly-ethylene glycols or their derivatives may be used as linkers, such as those disclosed in Maskos, U. & Southern, E.M. Nucleic Acids Research 20: 1679-1684, 1992. Succinic acid based linkers are also widely used, although these are less preferred for applications involving the labelling of oligonucleotides as they are generally base labile and are thus incompatible with the base mediated de-protection steps used in a number of oligonucleotide synthesisers.

Propargylic alcohol is a bifunctional linker that provides a linkage that is stable under the conditions of oligonucleotide synthesis and is a preferred linker for use with this invention in relation to oligonucleotide applications. Similarly 6-aminohexanol is a useful bifunctional reagent to link appropriately functionalised molecules and is also a preferred linker.

A variety of known cleavable linker groups may be used in conjunction with the compounds employed in this invention, such as photocleavable linkers. Ortho-nitrobenzyl groups are known as photocleavable linkers, particularly 2-nitrobenzyl esters and 2-nitrobenzylamines, which cleave at the benzylamine bond. For a review on cleavable linkers see Lloyd-Williams et al., Tetrahedron 49, 11065-11133, 1993, which covers a variety of photocleavable and chemically cleavable linkers.

WO 00/02895 discloses the vinyl sulphone compounds as cleavable linkers, which are also applicable for use with this invention, particularly in applications involving the labelling of polypeptides, peptides and amino acids. The content of this application is incorporated by reference.

WO 00/02895 discloses the use of silicon compounds as linkers that are cleavable by base in the gas phase. These linkers are also applicable for use with this invention, particularly in applications involving the labelling of oligonucleotides. The content of this application is incorporated by reference.

Mass Normalisation Moiety

The structure of the mass normalization moiety of the mass label used in the present invention is not particularly limited provided that it is suitable for ensuring that the mass label has a desired aggregate mass. However, the mass normalization moiety preferably comprises a straight or branched C$_1$-C$_{20}$ substituted or unsubstituted aliphatic group and/or one or more substituted or unsubstituted amino acids.

Preferably, the mass normalization moiety comprises a C$_1$-C$_6$ substituted or unsubstituted aliphatic group, more preferably a $C_1$, $C_2$, $C_3$, $C_4$, $C_5$ substituted or unsubstituted aliphatic group, still more preferably a $C_1$, $C_2$, or $C_5$ substituted or unsubstituted aliphatic group or a $C_1$ methyl substituted group.

The one or more substituted or unsubstituted amino acids may be any essential or non-essential naturally occurring amino acids or non-naturally occurring amino acids. Preferred amino acids are alanine, β-alanine and glycine.

The substituents of the mass normalisation moiety are not particularly limited and may comprise any organic group and/or one or more atoms from any of groups IIIA, IVA, VA, VIA or VIIA of the Periodic Table, such as a B, Si, N, P, O, or S atom or a halogen atom (e.g. F, Cl, Br or I).

When the substituent comprises an organic group, the organic group preferably comprises a hydrocarbon group. The hydrocarbon group may comprise a straight chain, a branched chain or a cyclic group. Independently, the hydrocarbon group may comprise an aliphatic or an aromatic group. Also independently, the hydrocarbon group may comprise a saturated or unsaturated group.

When the hydrocarbon comprises an unsaturated group, it may comprise one or more alkene functionalities and/or one or more alkyne functionalities. When the hydrocarbon comprises a straight or branched chain group, it may comprise one or more primary, secondary and/or tertiary alkyl groups. When the hydrocarbon comprises a cyclic group it may comprise an aromatic ring, an aliphatic ring, a heterocyclic group, and/or fused ring derivatives of these groups. The cyclic group may thus comprise a benzene, naphthalene, anthracene, indene, fluorene, pyridine, quinoline, thiophene, benzothiophene, furan, benzofuran, pyrrole, indole, imidazole, thiazole, and/or an oxazole group, as well as regioisomers of the above groups.

The number of carbon atoms in the hydrocarbon group is not especially limited, but preferably the hydrocarbon group comprises from 1-40 C atoms. The hydrocarbon group may thus be a lower hydrocarbon (1-6 C atoms) or a higher hydrocarbon (7 C atoms or more, e.g. 7-40 C atoms). The number of atoms in the ring of the cyclic group is not especially limited, but preferably the ring of the cyclic group comprises from 3-10 atoms, such as 3, 4, 5, 6 or 7 atoms.

The groups comprising heteroatoms described above, as well as any of the other groups defined above, may comprise one or more heteroatoms from any of groups IIIA, IVA, VA, VIA or VIIA of the Periodic Table, such as a B, Si, N, P, O, or S atom or a halogen atom (e.g. F, Cl, Br or I). Thus the substituent may comprise one or more of any of the common functional groups in organic chemistry, such as hydroxy groups, carboxylic acid groups, ester groups, ether groups, aldehyde groups, ketone groups, amine groups, amide groups, imine groups, thiol groups, thioether groups, sulphate groups, sulphonic acid groups, and phosphate groups etc. The substituent may also comprise derivatives of these groups, such as carboxylic acid anhydrydes and carboxylic acid halides.

In addition, any substituent may comprise a combination of two or more of the substituents and/or functional groups defined above.

Reactive Mass Label

The reactive mass labels typically used in the present invention for labelling and detecting a biological molecule by mass spectroscopy comprise a reactive functionality for facilitating attachment of or for attaching the mass label to a biological molecule and a mass label as defined above. In preferred embodiments of the present invention, the reactive functionality allows the mass label to be reacted covalently to an analyte, preferably an amino acid, peptide or polypeptide. The reactive functionality may be attached to the mass labels via a linker which may or may not be cleavable. The reactive functionality may be attached to the mass marker moiety of the mass label or the mass normalization moiety of the mass label.

A variety of reactive functionalities may be introduced into the mass labels used in this invention. The structure of the reactive functionality is not particularly limited provided that it is capable of reacting with one or more reactive sites on the biological molecule to be labelled. The reactive functionality is preferably a nucleophile or an electrophile.

In the simplest embodiments this may be an N-hydroxysuccinimide ester. An N-hydroxysuccinimide activated mass label could also be reacted with hydrazine to give a hydrazide reactive functionality, which can be used to label periodate oxidised sugar moieties, for example. Amino-groups or thiols can be used as reactive functionalities in some applications. Lysine can be used to couple mass labels to free carboxyl functionalities using a carbodiimide as a coupling reagent. Lysine can also be used as the starting point for the introduction of other reactive functionalities into the mass labels of this invention. The thiol-reactive maleimide functionality can be introduced by reaction of the lysine epsilon amino group with maleic anhydride. The cysteine thiol group can be used as the starting point for the synthesis of a variety of alkenyl sulphone compounds, which are useful protein labelling reagents that react with thiols and amines. Compounds such as aminohexanoic acid can be used to provide a spacer between the mass modified mass marker moiety or mass normalization moiety and the reactive functionality.

Table 1 below lists some reactive functionalities that may be reacted with nucleophilic functionalities which are found in biomolecules to generate a covalent linkage between the two entities. Any of the functionalities listed below could be introduced into the compounds of this invention to permit the mass markers to be attached to a biological molecule of interest. A reactive functionality can be used to introduce a further linker groups with a further reactive functionality if that is desired. Table 1 is not intended to be exhaustive and the present invention is not limited to the use of only the listed functionalities.

TABLE 1

| Nucleophilic Functionality | Reactive Functionality | Resultant Linking Group |
|---|---|---|
| —SH | —SO$_2$—CH=CR$_2$ | —S—CR$_2$—CH$_2$—SO$_2$— |
| —NH$_2$ | —SO$_2$—CH=CR$_2$ | —N(CR$_2$—CH$_2$—SO$_2$—)$_2$ or —NH—CR$_2$—CH$_2$—SO$_2$— |
| —NH$_2$ | 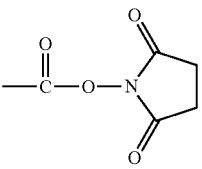 | —CO—NH— |
| —NH$_2$ | 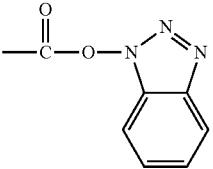 | —CO—NH— |

TABLE 1-continued

| Nucleophilic Functionality | Reactive Functionality | Resultant Linking Group |
|---|---|---|
| —NH$_2$ | —NCO | —NH—CO—NH— |
| —NH$_2$ | —NCS | —NH—CS—NH— |
| —NH$_2$ | —CHO | —CH$_2$—NH— |
| —NH$_2$ | —SO$_2$Cl | —SO$_2$—NH— |
| —NH$_2$ | —CH═CH— | —NH—CH$_2$—CH$_2$— |
| —OH | —OP(NCH(CH$_3$)$_2$)$_2$ | —OP(═O)(O)O— |

In a preferred embodiment of the present invention the reactive functionality comprises the following group:

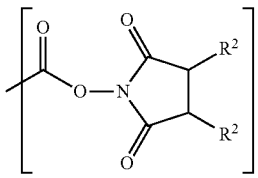

wherein each R$^2$ is independently H, a substituted or unsubstituted straight or branched C$_1$-C$_6$ alkyl group, a substituted or unsubstituted aliphatic cyclic group, a substituted or unsubstituted aromatic group or a substituted or unsubstituted heterocyclic group.

The substituents of the reactive functionality are not particularly limited and may comprise any organic group and/or one or more atoms from any of groups IIIA, IVA, VA, VIA or VIIA of the Periodic Table, such as a B, Si, N, P, O, or S atom or a halogen atom (e.g. F, Cl, Br or I).

When the substituent comprises an organic group, the organic group preferably comprises a hydrocarbon group. The hydrocarbon group may comprise a straight chain, a branched chain or a cyclic group. Independently, the hydrocarbon group may comprise an aliphatic or an aromatic group. Also independently, the hydrocarbon group may comprise a saturated or unsaturated group.

When the hydrocarbon comprises an unsaturated group, it may comprise one or more alkene functionalities and/or one or more alkyne functionalities. When the hydrocarbon comprises a straight or branched chain group, it may comprise one or more primary, secondary and/or tertiary alkyl groups. When the hydrocarbon comprises a cyclic group it may comprise an aromatic ring, an aliphatic ring, a heterocyclic group, and/or fused ring derivatives of these groups. The cyclic group may thus comprise a benzene, naphthalene, anthracene, indene, fluorene, pyridine, quinoline, thiophene, benzothiophene, furan, benzofuran, pyrrole, indole, imidazole, thiazole, and/or an oxazole group, as well as regioisomers of the above groups.

The number of carbon atoms in the hydrocarbon group is not especially limited, but preferably the hydrocarbon group comprises from 1-40 C atoms. The hydrocarbon group may thus be a lower hydrocarbon (1-6 C atoms) or a higher hydrocarbon (7 C atoms or more, e.g. 7-40 C atoms). The number of atoms in the ring of the cyclic group is not especially limited, but preferably the ring of the cyclic group comprises from 3-10 atoms, such as 3, 4, 5, 6 or 7 atoms.

The groups comprising heteroatoms described above, as well as any of the other groups defined above, may comprise one or more heteroatoms from any of groups IIIA, IVA, VA, VIA or VIIA of the Periodic Table, such as a B, Si, N, P, O, or S atom or a halogen atom (e.g. F, Cl, Br or I). Thus the substituent may comprise one or more of any of the common functional groups in organic chemistry, such as hydroxy groups, carboxylic acid groups, ester groups, ether groups, aldehyde groups, ketone groups, amine groups, amide groups, imine groups, thiol groups, thioether groups, sulphate groups, sulphonic acid groups, and phosphate groups etc. The substituent may also comprise derivatives of these groups, such as carboxylic acid anhydrydes and carboxylic acid halides.

In addition, any substituent may comprise a combination of two or more of the substituents and/or functional groups defined above.

In a more preferred embodiment the reactive functionality comprises the following group:

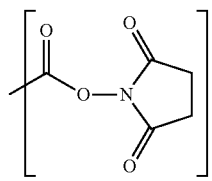

In a preferred embodiment of the present invention the reactive mass label has one of the following structures:

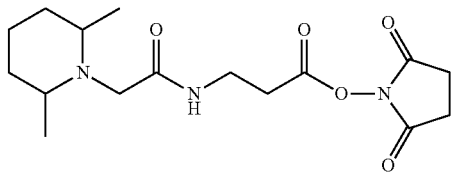

3-[2-(2,6-Dimethyl-piperidin-1-yl)-acetylamino]-propanoic acid-(2,5-dioxo-pyrrolidine-1-yl)-ester (DMPip-βAla-OSu)

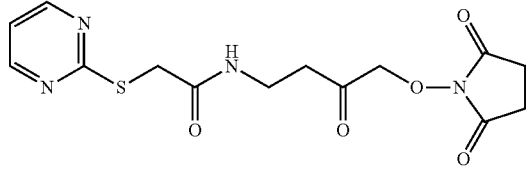

3-[2-(Pyrimidin-2-ylsulfanyl)-acetylamino]-propanoic acid-(2,5-dioxopyrrolidine-1-yl)-ester (Pyrm-βAla-OSu)

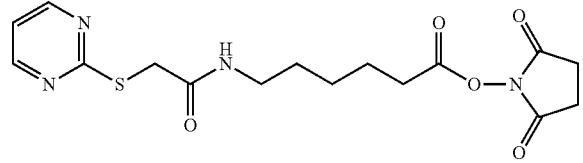

6-[(Pyrimidin-2-ylsulfanyl)-acetylamino]-hexanoic acid-(2,5-dioxopyrrolidine-1-yl)-ester (Pyrm-C6-OSu)

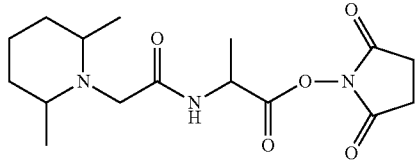

2-[2-(2,6-Dimethyl-piperidin-1-yl)-acetylamino]-propanoic acid-(2,5-dioxo-pyrrolidine-1-yl)-ester (DMPip-Ala-OSu)

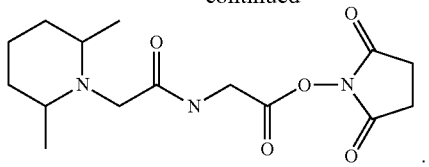

2-[2-(2,6-Dimethyl-piperidin-1-yl)-acetylamino]-
acetic acid-(2,5-dioxo-pyrrolidine-1-yl)-ester
(Pyrm-Gly-OSu)

In the method according to the present invention, each label in the set has a common aggregate mass and each label in the set has a mass marker moiety of a unique mass.

It is preferred that, each mass marker moiety in the set has a common basic structure and each mass normalisation moiety in the set has a common basic structure, and each mass label in the set comprises one or more mass adjuster moieties, the mass adjuster moieties being attached to or situated within the basic structure of the mass marker moiety and/or the basic structure of the mass normalisation moiety. In this embodiment, every mass marker moiety in the set comprises a different number of mass adjuster moieties and every mass label in the set has the same number of mass adjuster moieties.

Throughout this description, by common basic structure, it is meant that two or more moieties share a structure which has substantially the same structural skeleton, backbone or core. The skeleton comprises the mass marker moiety of the formula given above or the mass normalisation moiety as defined above. The skeleton may additionally comprise a number of amino acids linked by amide bonds. Other units such as aryl ether units may also be present. The skeleton or backbone may comprise substituents pendent from it, or atomic or isotopic replacements within it, without changing the common basic structure.

In a preferred embodiment the set of mass labels or reactive mass labels according to the invention comprise mass labels having the following structure:

$$M(A)_y\text{-}L\text{-}X(A)_z$$

wherein M is a mass normalisation moiety, X is a mass marker moiety, A is a mass adjuster moiety, L is a cleavable linker, y and z are integers of 0 or greater, and y+z is an integer of 1 or greater. Preferably M is a fragmentation resistant group, L is a linker that is susceptible to fragmentation on collision with another molecule or atom and X is preferably a pre-ionised, fragmentation resistant group.

The sum of the masses of M and X is the same for all members of the set. Preferably M and X have the same basic structure or core structure, this structure being modified by the mass adjuster moieties. The mass adjuster moiety ensures that the sum of the masses of M and X is the same for all mass labels in a set, but ensures that each X has a distinct (unique) mass.

The mass adjuster moiety (A) is preferably selected from:
(a) an isotopic substituent situated within the mass marker moiety and/or within the mass normalisation moiety, and
(b) substituent atoms or groups attached to the mass marker moiety and/or attached to the mass normalisation moiety.

Preferably the mass adjuster moiety is selected from a halogen atom substituent, a methyl group substituent, and $^{2}H$, $^{15}N$, $^{18}O$, or $^{13}C$ isotopic substituents.

In one preferred embodiment the present invention, each mass label in the set of mass labels as defined above has the following structure:

$$X^{(*)n}\text{-}L\text{-}M^{(*)m}$$

wherein X is the mass marker moiety, L is the cleavable linker, M is the mass normalisation moiety, * is an isotopic mass adjuster moiety, and n and m are integers of 0 or greater such that each label in the set comprises a mass marker moiety having a unique mass and each label in the set has a common aggregate mass.

It is preferred that X comprises the following group:

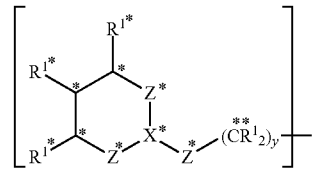

wherein $R^1$, Z, X and y are as defined above and each label in the set comprises 0, 1 or more * such that each label in the set comprises a mass marker moiety having a unique mass and each label in the set has a common aggregate mass.

In a further preferred embodiment, the reactive mass labels of the present invention comprise the following reactive functionality group:

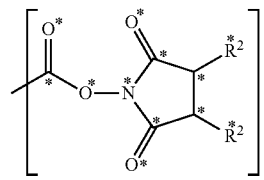

wherein $R^2$ is as defined above and the set comprises 0, 1 or more * such that each label in the set comprises a mass marker moiety having a unique mass and each label in the set has a common aggregate mass.

In all of the above preferred formulae, it is particularly preferred that the isotopic species * is situated within the mass marker moiety and/or the linker and/or the mass adjuster moiety, rather than on any reactive moiety that is present to facilitate attaching the label to an analyte. The number of isotopic substituents is not especially limited and can be determined depending on the number of labels in the set. Typically, the number of * species is from 0-20, more preferably from 0-15 and most preferably from 1-10, e.g. 1, 2, 3, 4, 5, 6, 7 or 8. In a set of two labels, it is preferred that the number of species * is 1, whilst in a set of 5 labels, it is preferred that the number is 4, whilst in a set of 6 labels it is preferred that the number is 5. However, the number may be varied depending upon the chemical structure of the label.

If desired, isotopic variants of S may also be employed as mass adjuster moieties, if the labels contain one or more sulphur atoms.

In a particularly preferred embodiment wherein the mass adjuster moiety is $^{15}N$ or $^{13}C$ the set of reactive mass labels comprises two mass labels having the following structures:

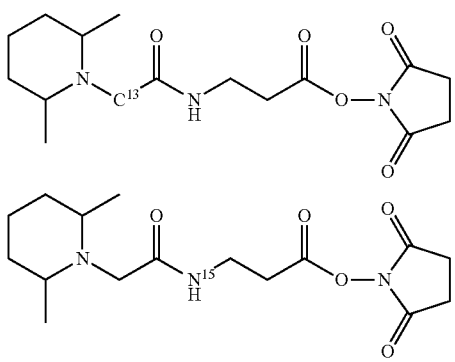

In an alternative particularly preferred embodiment wherein the mass adjuster moiety is $^{15}N$ or $^{13}C$ the set of reactive mass labels comprises the set comprises five mass labels having the following structures:

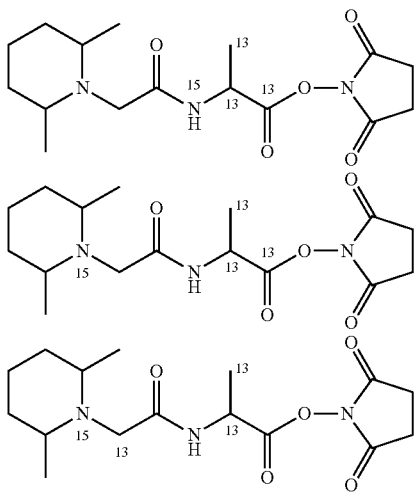

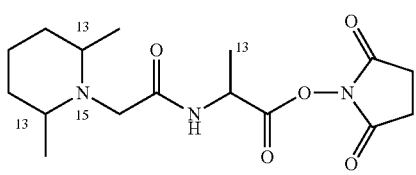

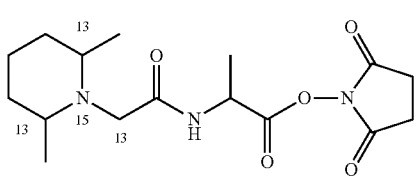

In an alternative particularly preferred embodiment wherein the mass adjuster moiety is $^{15}N$ or $^{13}C$ the set of reactive mass labels comprises six mass labels I-VI having the following structures, or stereoisomers of these structures:

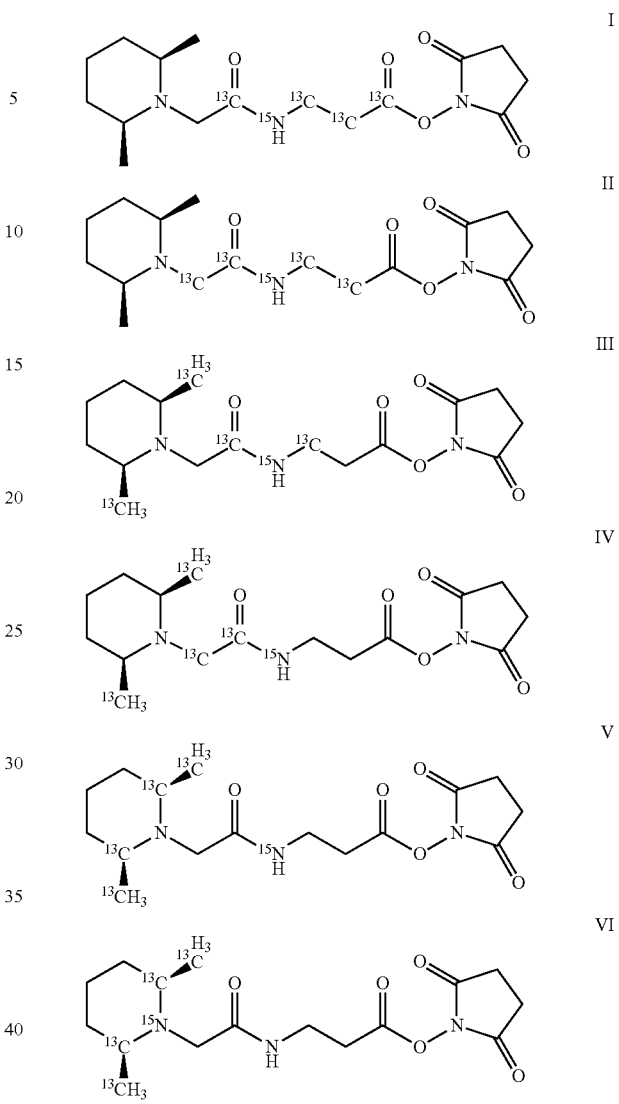

The method according to the present invention may comprise a further step of separating the components of the samples prior to step (a). The method may also comprise a step of digesting each sample with at least one enzyme to digest components of the samples prior to step (a). The enzyme digestion step may also occur after step (a) but before step (b).

In a further embodiment, the mass labels used in the method further comprise an affinity capture ligand. The affinity capture ligand of the mass label binds to a counter-ligand so as to separate the isobarically labeled analytes from the unlabelled analytes after step (a) but before step (b).

Affinity capture ligands are ligands which have highly specific binding partners. These binding partners allow molecules tagged with the ligand to be selectively captured by the binding partner. Preferably a solid support is derivitised with the binding partner so that affinity ligand tagged molecules can be selectively captured onto the solid phase support. A preferred affinity capture ligand is biotin, which can be introduced into the mass labels of this invention by standard methods known in the art. In particular a lysine residue may be incorporated after the mass marker moiety or mass normalization moiety through which an amine-reactive biotin can be linked to the mass labels (see for example Geahlen R. L. et al., Anal Biochem 202(1): 68-67, "A general method for preparation of peptides biotinylated at the carboxy terminus." 1992; Sawutz D. G. et al., Peptides 12(5): 1019-1012, "Synthesis and molecular characterization of a biotinylated analogue of [Lys]bradykinin." 1991; Natarajan S. et al., Int J Pept Protein Res 40(6): 567-567, "Site-specific biotinylation. A novel approach and its application to endothelin-1 analogues and PTH-analogue.", 1992). Iminobiotin is also applicable. A variety of avidin counter-ligands for biotin are available, which include monomeric and tetrameric avidin and streptavidin, all of which are available on a number of solid supports.

Other affinity capture ligands include digoxigenin, fluorescein, nitrophenyl moieties and a number of peptide epitopes, such as the c-myc epitope, for which selective monoclonal antibodies exist as counter-ligands. Metal ion binding ligands such as hexahistidine, which readily binds $Ni^{2+}$ ions, are also applicable. Chromatographic resins, which present iminodiacetic acid chelated $Ni^{2+}$ ions are commercially available, for example. These immobilised nickel columns may be used to capture mass labels. As a further alternative, an affinity capture functionality may be selectively reactive with an appropriately derivatised solid phase support. Boronic acid, for example, is known to selectively react with vicinal cis-diols and chemically similar ligands, such as salicylhydroxamic acid.

The method according to the invention may further include the step of separating the isobarically labeled analytes electrophoretically or chromatographically after step (a) but before step (b). In a preferred embodiment, strong cation exchange chromatography is used.

The term "test sample" refers to any specimen in which an analyte may be present. The test sample may comprise only one analyte. Alternatively, the test sample may comprise a plurality of different analytes. In this embodiment, a calibration sample is provided for each different analyte. The test sample may be from a natural source or may be produced synthetically. An example of a synthetic sample is a mixture of recombinant proteins. In one embodiment, the test sample is a complex mixture, for example a sample from a plant or an animal. In a preferred embodiment the sample is from a human.

Examples of test samples assayed in the present invention include: mammalian tissue, fluids such as blood, plasma, serum cerebrospinal fluid, synovial fluid, ocular fluid, urine, tears and tear duct exudate, lung aspirates including bronchoalveolar lavage fluid, breast milk, nipple aspirate, semen, lavage fluids, cell extracts, cell lines and sub-cellular organelles, tissues such as solid organ tissues, cell culture supernatants or preparations derived from mammals, fish, birds, insects, annelids, protozoa and bacteria, tissue culture extracts, plant tissues, plant fluids, plant cell culture extracts, bacteria, viruses, fungi, fermentation broths, foodstuffs, pharmaceuticals and any intermediary products.

In a preferred embodiment the test sample is blood plasma. In a particularly preferred embodiment the test sample is depleted blood plasma. This is blood plasma which has been purified to remove the most abundant plasma proteins, such as albumin, so as to reduce the protein load in the sample, hence reducing the number of analytes in the sample.

The term "calibration sample" refers to a sample which comprises at least two different aliquots of the analyte. The different aliquots each have a known quantity of the analyte. The term "known quantity" means that the absolute quantity, or a qualitative quantity of the analyte in each aliquot of the calibration sample is known. A qualitative quantity in the present context means a quantity which is not known absolutely, but may be a range of quantities that are expected in a subject having a particular state, for example a subject in a healthy or diseased state, or some other expected range depending on the type of test sample under investigation.

Each aliquot is "different" since it contains a different quantity of the analyte. Typically this is achieved by taking different volumes from a standard sample, especially for qualitative quantities where taking different volumes will ensure that different quantities are present in each aliquot in a desired ratio, without needing to know the absolute quantities. As an alternative, each aliquot is prepared separately and is not taken from the same sample. In one embodiment, each different aliquot has the same volume, but comprises a different quantity of the analyte.

The calibration sample may be a natural sample such as a body fluid or a tissue extract or may be synthetic, as for the sample to be assayed. The calibration sample may comprise a recombinantly expressed protein, synthetically manufactured peptide or oligonucleotide. In addition it is possible to produce a number of different peptides by recombinant protein expression in a concatenated sequence. European patent application EP 1736480 discloses methods of producing multiple reference peptides as a concatenated recombinant protein for use in multiple reaction monitoring experiments in a manner analogous to the AQUA methodology. Such methods of production may be combined with isobaric mass labels to provide the calibration samples according to any of the various aspects of this invention.

The calibration sample may be a standardised form of the sample to be assayed. The calibration sample may comprise all of the components of the sample to be assayed but in particular quantities. For example, the calibration sample may comprise a standardised preparation of mammalian tissue, fluids such as blood, plasma, serum cerebrospinal fluid, synovial fluid, ocular fluid, urine, tears and tear duct exudate, lung aspirates including bronchoalveolar lavage fluid, breast milk, nipple aspirate, semen, lavage fluids, cell extracts, cell lines and sub-cellular organelles, tissues such as solid organ tissues, cell culture supernatants or preparations derived from mammals, fish, birds, insects, annelids, protozoa and bacteria, tissue culture extracts, plant tissues, plant fluids, plant cell culture extracts, bacteria, viruses, fungi, fermentation broths, foodstuffs, pharmaceuticals and any intermediary products. If the analytes of interest are proteins, since all proteins in the calibration sample are labelled, the entire proteome of such a sample may be used as a reference for all proteins of the study sample.

Alternatively, the calibration sample may comprise only analytes to be assayed in the sample, and not any other components of the sample. The calibration sample comprising one or more analytes may be produced and isobarically labelled exogenously and added to the complex mixture containing the analyte. For example, if the sample is a plasma sample, but only a particular protein is to be assayed in the plasma sample, a calibration sample can be prepared which comprises different aliquots of the recombinant form of the protein.

In a method according to the invention, the quantity of analyte in each aliquot in the calibration sample is a known absolute quantity. This allows for the absolute quantity of an analyte in a test sample to be determined in step (b).

In an alternative method, the absolute quantity of an analyte in each aliquot in the calibration sample is not known. In this embodiment, the quantity of analyte in each aliquot in the calibration sample is a known qualitative quantity. The calibrating step comprises calibrating the quantity of the analyte in the test sample against the qualitative and determined quantities of the analytes in the aliquots of the calibration sample. In a particular embodiment, the qualitative quantity is an expected range of quantities of analyte in a subject having a particular state, such as a healthy or diseased state. Assays which provide such calibration samples for relative quantitation have wide range of applications including biomarker discovery, industrial microbiology, pharmaceutical and food manufacture and the diagnosis and management of human and veterinary disease Relative quantitation experiments are often useful when analysing complex biological samples such as blood plasma. In a specific embodiment, a large amount of entire human blood plasma is split into several (i.e. four) aliquots and individually labelled with different isobaric mass labels. For instance, one could utilise the 6-plex Tandem Mass Tag reagents (see above) to produce four labelled aliquots of blood plasma. 6TMT-128, 6TMT-129, 6TMT-130, 6TMT-131 would be used for labelling. All individual samples of a blood plasma study are labelled with one further different version of this isobaric mass tag, i.e. 6TMT-126. The aliquots of blood plasma can now be used to generate a calibration curve, for instance by mixing the 4 aliquots in a 0.5 to 1 to 2 to 5 µL ratio to produce a calibration sample, and then adding 1 µl of the study sample. By combining the sample with the calibration sample comprising four differentially labelled aliquots, virtually all MS/MS experiments performed with this material will result in groups of five reporter-ions—four from the calibration sample and one from the sample. Thus, the entire proteome can be used in a 4-point calibration curve. If all plasma samples of the study are spiked with the identical amount of the calibration sample, relative quantification across all study samples becomes possible. Since the calibration sample can be used by multiple laboratories, cross-study and cross-laboratory comparisons are possible.

Whereas the absolute quantity of an analyte might not be known, the % change in quantity can be calculated from the calibration curve. Depending on the application, the ratio and width of the calibration curve can be adjusted.

In a preferred embodiment, the quantity of analyte in each different aliquot of the calibration sample is selected to reflect the known or suspected variation of the analyte in the test sample. In a still further preferred embodiment, aliquots are provided which comprise the analyte in quantities which correspond to the upper and lower limits, and optionally intermediate points within a range of the known or suspected quantities of the analyte found in test samples of healthy or diseased subjects.

Because each analyte is quantified independently of all other analytes in the sample it is conceivable to prepare multiple sets of calibration samples each at widely different concentrations to all other calibration samples, so enhancing the dynamic range of the experiment. It is also possible to prepare a number of reference biomolecules for each analyte wherein each biomolecule is provided in a range of overlapping quantities thereby extending the total range of the standard curve for a given analyte. As an example a number of different tryptic peptides from a target protein may be selected for use as reference standards based on their performance in a tandem mass spectrometer. The reference peptides may be selected on the basis of the ion intensity of the ion corresponding to the peptide in a mass spectrum or on the basis of the signal-to-noise ratio in the area of the spectrum in which the ion corresponding to the peptide appears. Alternatively the reference peptides may be selected so as to avoid peptides which have isobaric species. The selection of proteotypic peptides, i.e. peptides which are only present in a particular protein is particularly favoured.

If each standard peptide is independently labelled with up to five different members of a sixplex set of isobaric mass tags these may be mixed in different ratios to provide a five-point standard curve. The same isobaric mass labels may be used to label second, third, fourth or more standard peptides each of which may be mixed in different ratios covering a range of concentrations different to that covered by each of the other reference peptides for the same analyte.

A different calibration curve is produced for each peptide derived from the target protein, each calibration curve covering a different range of concentrations. The concentration of each peptide is then determined from their respective calibration curve, and this can be related back to the concentration of the target protein. For some of the calibration curves, the quantity of the peptide in the test sample may fall in the middle of the calibration curve, providing an accurate determination of its actual quantity in the sample. For other calibration curves covering a different range in concentrations, the quantity of the peptide in the test sample may fall outside the range of the calibration curve. By using multiple peptides which are each derived from a single analyte of interest, we can produce multiple calibration curves which can be related to the same analyte and then choose the most accurate calibration to determine the concentration of the analyte in the test sample from the concentration of one or more of the peptides. In this way a broad dynamic range may be covered without compromising assay sensitivity.

The calibration sample may comprise a normal quantity of an analyte. The quantity of the analyte in the calibration sample may indicate that a plant, animal, or preferably a human is healthy. Alternatively, the calibration sample may comprise an analyte in a quantity that indicates the presence and/or stage of a particular disease. In a further embodiment, the calibration sample comprises an analyte in a quantity that indicates the efficacy and/or toxicity of a therapy. Standard panels of known markers of a particular trait such as presence and/or stage of disease, response to therapy, and/or toxicity are prepared. Calibration samples comprising body fluids or tissue extracts labelled with an isobaric mass tag could be prepared from patients with well characterised disease including but not limited to tumours, neurodegeneration, cardiovascular, renal, hepatic, respiratory, metabolic, inflammatory, and infectious diseases. Known amounts of such samples are added to multiple test samples in such a manner that for a series of analyses ion intensities in the MS/MS scan can be normalised based on the ion intensity of the common calibration sample, thereby providing more accurate comparisons between the separate analyses, reducing the analytical variability of the study.

In the case of coronary medicine a series of peptides derived from the tryptic digestion of known heart disease markers such as myoglobin, troponin-I, CK-MB, BNP, pro-BNP and NT-pro-BNP are produced synthetically and split into three aliquots. Each aliquot of each reference peptide is labelled with one of three isobaric mass tags from a set of such isobaric mass tags wherein all tags in the set have substantially the same aggregate mass as determined by mass spectrometry and wherein each tag in the set releases a mass reporter ion of unique mass on collision induced dissociation in a mass spectrometer. Each unique reference peptide-mass tag molecule is then added to a carrier solution such as a MS-compatible buffer at a known concentration such that the concentration of the three differentially labelled aliquots of the same reference peptide are different, and that the differences span the normal biological concentrations of the parent protein in patients with cardiac disease. The resultant reference peptide panel is added at a defined volumetric ratio with a test sample that has been labelled with a fourth isobaric mass tag from the same set of isobaric mass tags used to label the reference peptides. The spiked sample is then subjected to tandem mass spectrometry wherein the survey scan is performed in a directed manner to only identify those precursor ions of characteristic retention time and mass correlating to each of the isobarically labelled reference peptides. For each selected ion the MS/MS scan will contain reporter ions derived from the high, medium and low concentration reference peptides and the test sample.

A simple standard curve is easily constructed from the reference peptide reporter ion intensities and the fourth reporter ion from the same peptide in the test sample can be read against the calibration curve. By this means the absolute concentration of multiple biologically relevant proteins can be determined in a single MS/MS experiment. The skilled artisan will be aware that the number of different proteins for which reference peptides are prepared need not be particularly limited and will be in the range of 1-100 and most preferably 1-50. Similarly the number of representative peptides may be in the range of 1-20, preferably 1-10, more preferably 1-5 and most preferably 1-3. It would be understood by the skilled artisan that the example described above is a general examplar and the principles described therein may be applied to known markers of any disease and applied for disease diagnosis, monitoring of disease progression or monitoring the response of a patient to treatment.

A further application is in the use of these calibration samples in time course experiments. The "Status" of a sample with respect to time course can be established if the (4) different aliquots are from 4 different time points, such as time zero, 1 hour, 8 hours, and 24 hours into an experiment (drug challenge in mice and man, induction of fermentation in E. coli and yeast), also on a longer time scale of weeks and months for development or treatment response of chronic diseases.

In a further aspect of the invention, one of the aliquots of the calibration sample comprises an analyte in a quantity which serves as a trigger during an MS scan or during non-scanning MS/MS to initiate an MS/MS scan.

Non-scanning MS/MS is when you do not select for any particular ion with a given m/z ratio in a mass analyser in a mass spectrometer, but instead essentially all of the analytes are fragmented to produce an unspecific fragment spectrum. Typically, this involves allowing all ions to pass from a first mass analyser into a collision cell, where CID occurs on all of the analytes in the sample instead of a particular selected ion as in conventional MS/MS.

Although the MS/MS spectrum will not be specific to a particular analyte, the reporter ion from the trigger can be used as an indicator that an analyte of interest is right now entering the mass spectrometer. In a preferred embodiment, the presence of a reporter ion from the trigger indicates that an analyte of interest is eluting from an LC column during LC-MS. This would "trigger" the execution of a pre-defined MS/MS experiment.

This trigger may not necessarily be an analyte labelled with an isobaric mass label. The trigger may be any other labelled analyte which co-elutes, or substantially co-elutes with the labelled analyte of interest during LC-MS. The label of the trigger analyte may have a different mass to that of the isobaric mass labels of the calibration sample. For example, in one embodiment, the calibration sample comprises aliquots of an analyte differentially labelled with isobaric mass labels, and further comprises an aliquot of the analyte which is labelled with a chemically identical but isotopically distinct mass label, preferably with a mass difference of 5 Da from that of the isobaric mass labels. The isotopically distinct mass label could then serve as the "trigger". During the MS phase of the analysis each analyte present in the calibration sample bearing the isotopically distinct and isobaric labels will appear as a pair of peaks separated by the mass difference between the isobaric and isotopically distinct labels and wherein the analyte bearing the isotopically distinct label is present in a readily detectable amount. The mass spectrometer is programmed to perform a dedicated MS/MS experiment on the isobarically labelled analyte in such pairs, thereby triggering the quantitative analysis of the analytes of interest.

In a preferred embodiment, the isotopically distinct mass label trigger comprises no isotopic substituents, and the isobaric mass labels comprise a plurality of isotopic substituents, preferably $^{2}H$, $^{15}N$, $^{18}O$, or $^{13}C$ isotopic substituents. This provides a mass difference between the analytes of the calibration sample labelled with isobaric mass labels and the analyte labelled with the trigger label. Since the trigger label comprises no isotopic substituents, this label can be used in large quantities if required without the need for costly isotope labelling.

The present invention also provides a method for increasing the detectability of low abundance analytes in a sample. For a low abundance protein of interest a recombinant reference protein may be expressed and then labelled with an isobaric mass tag. A test sample is then labelled with a second member of the same set of isobaric mass labels and a large amount of the isobarically labelled recombinant reference protein is added to the test sample at such a concentration as to be readily detectable by any chosen method which might include one- or two-dimensional gel electrophoresis, free-flow electrophoresis, capillary electrophoresis, off-gel isoelectric focussing and LC-MS/MS, LC-MS$^n$ and/or LC-TOF/TOF. Subsequent to detection of the isobarically labelled reference material a MS/MS scan or TOF/TOF analysis is performed and the reporter masses of the reference material and test sample are quantified. By using several members of a set of isobaric mass tags it is possible to provide a multipoint calibration curve with more physiologically relevant concentrations and so improving the overall accuracy of the analysis. A non-isobaric label can also be used to label the trigger analyte in this embodiment if it can be detected together with the labelled analytes of interest, for example if the trigger analyte and isobarically labelled analytes appear at the same spot on a gel or co-elute during LC-MS.

The Invention is described by the following non-limiting examples.

Example 1. Preparation of a Four Point Absolute Quantitative Standard for Bovine Serum Albumin To demonstrate the principle of the invention a set of reference reagents for bovine serum albumin (BSA) were prepared. One milligram of BSA was dissolved in buffer, reduced, alkylated and then digested by trypsin. The skilled artisan would appreciate that any method suitable of preparing tryptic peptides compatible for analysis by tandem mass spectrometry may be used.

The tryptic digest was split into four aliquots and each aliquot was labelled with a different member of the sixplex TMT labels of WO 2007/012849 whereby the first aliquot was labelled with the TMT label whose mass marker moiety has a mass of 128 Da, the second aliquot with the TMT label whose mass marker moiety has a mass of 129 Da, the third aliquot with the TMT label whose mass marker moiety has a mass of 130 Da and the final aliquot with the TMT label whose mass marker moiety has a mass of 131 Da. Labelling was performed by adding each respective TMT label reagent stock solutions (60 mM in acetonitrile) to the respective sample to give a final concentration of 15 mM TMT reagent. Samples were then incubated at room temperature for 1 hour. Finally, each sample was treated to reverse partial side reactions and pooling of labelled samples by adding hydroxylamine stock (50% w/v in water) to each protein sample (to reach a final concentration of 0.25% [w/v] hydroxylamine) and incubated at room temperature for 15 min.

To provide the BSA reference standard the different aliquots of TMT-labelled digests were mixed to give the following final concentrations:

| | |
|---|---|
| 128-TMT | 15.6 µg ml$^{-1}$ |
| 129-TMT | 46.9 µg ml$^{-1}$ |
| 130-TMT | 140.6 µg ml$^{-1}$ |
| 131-TMT | 421.9 µg ml$^{-1}$ |

For each analysis 10 µl of reference material is spiked into the analytical sample thereby providing reference amounts of 0.156, 0.469, 1.406 and 4.219 µg.

Example 2. Analysis of Bovine Serum Albumin Solutions by Tandem Mass Spectrometry The accuracy of quantitation of the BSA standard prepared in Example 1 was determined by analyzing a series of solutions of known BSA concentration into which the BSA standard solution was spiked.

Individual solutions of BSA were prepared in [Buffer] and treated as described above to prepare tryptic digests. Each tryptic digest was labelled essentially as described above using the TMT label whose mass marker moiety has a mass of 126 Da.

Prior to analysis by tandem mass spectrometry 10 µl of BSA standard stock solution was added to 10 µl of each 126-TMT labelled BSA solution and the total volume injected into the ionisation source of the QTOF II electrospray mass spectrometer.

LC-ESI-MS Protocol

Figure 2:
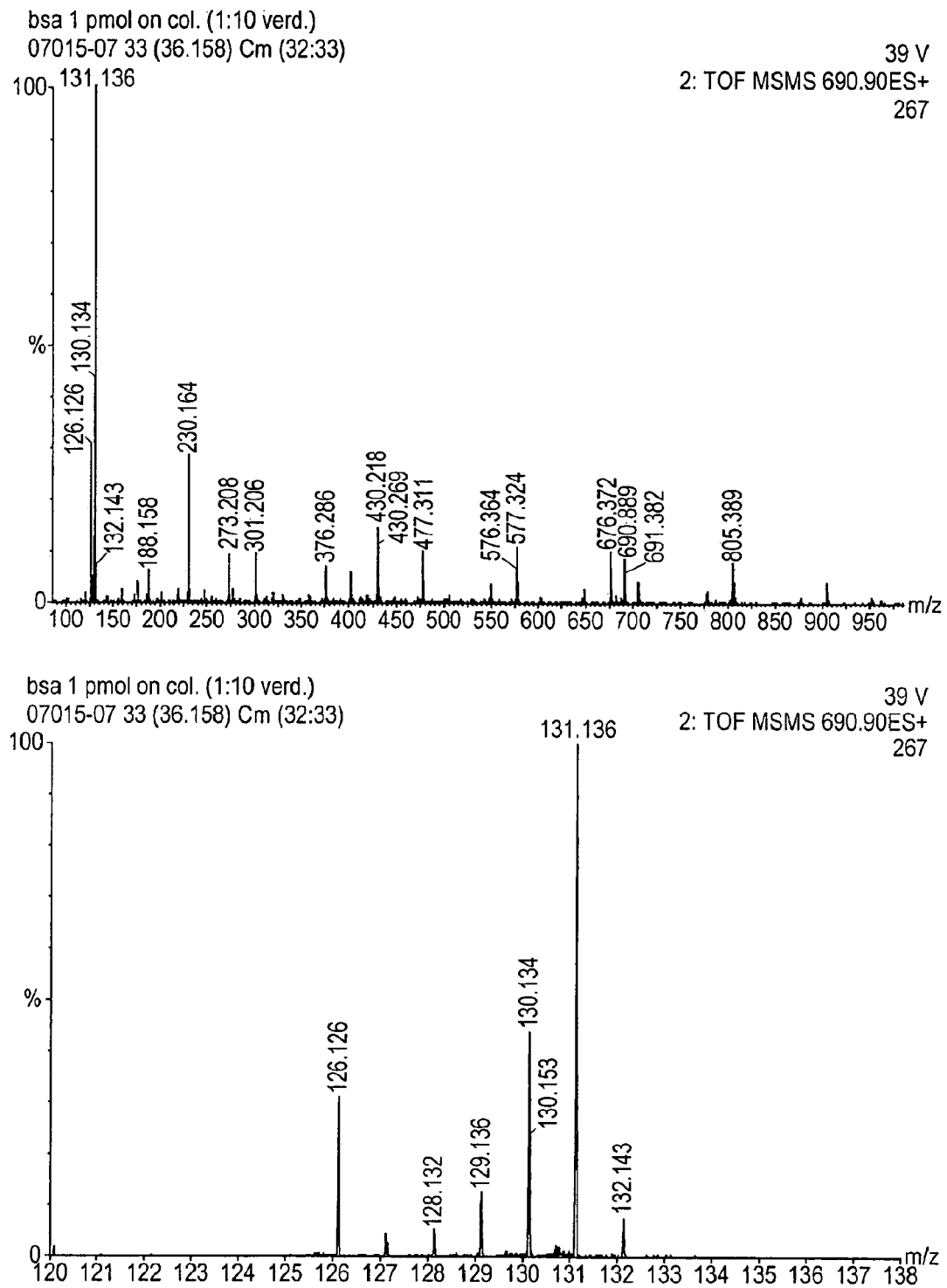
FIG. 2 shows the MS/MS profile of one BSA tryptic peptide. Upper panel shows the full MS/MS spectrum. Lower panel shows an expansion of the isobaric mass marker moiety region, the different intensities reflecting different abundances of the same peptide in the study sample (126) and calibration sample (128, 129, 130, 131).

MS/MS data were generated via our pipeline consisting of a Waters Cap-LC with 75 µm, 150 mm RP-C18 column with 3 µm particle size, flow rate 300 µl/min coupled to Micromass QToF II. MS/MS experiments were performed by data dependent acquisition (DDA). During the run, MS/MS experiments were done using acquisition time of 1.0 sec. for an MS-scan followed by 4 consecutive MS/MS scans of the four most abundant ion species of 1.4 sec. each. FIG. 2 shows an MS/MS profile for BSA tryptic peptide AEFVEVTK. Upper panel shows the full MS/MS spectrum. Lower panel shows zoom of isobaric mass marker moiety region and the different intensities reflecting different abundance of the same peptide in the study sample (126) and reference material (128, 129, 130 & 131).

MS/MS spectra are then analysed by Sequest™ and matched to an actual release of IPI database. Protein ID (accession number plus partial sequence as extracted from MS/MS scan), retention times, as well as reporter ion intensities of all reporters (126, 128, 129, 130 & 131 Da) are exported into an excel spreadsheet.

Depending on experimental conditions and the individual behaviour of a peptide during analysis, the selection of 1, 4, 10 or more peptides to participate in quantification is done. Preferably, peptides with low intensity reporters are excluded if their analytical precision and quality are questionable, as well as peptides where reporters are outside of defined intensity thresholds.

The results of the analysis of 10 µl of a BSA solution containing 100 µg ml$^{-1}$ 126-TMT labelled BSA spiked with 10 µl of the four point BSA reference standard described above are shown in Table 2.

Figure 3:
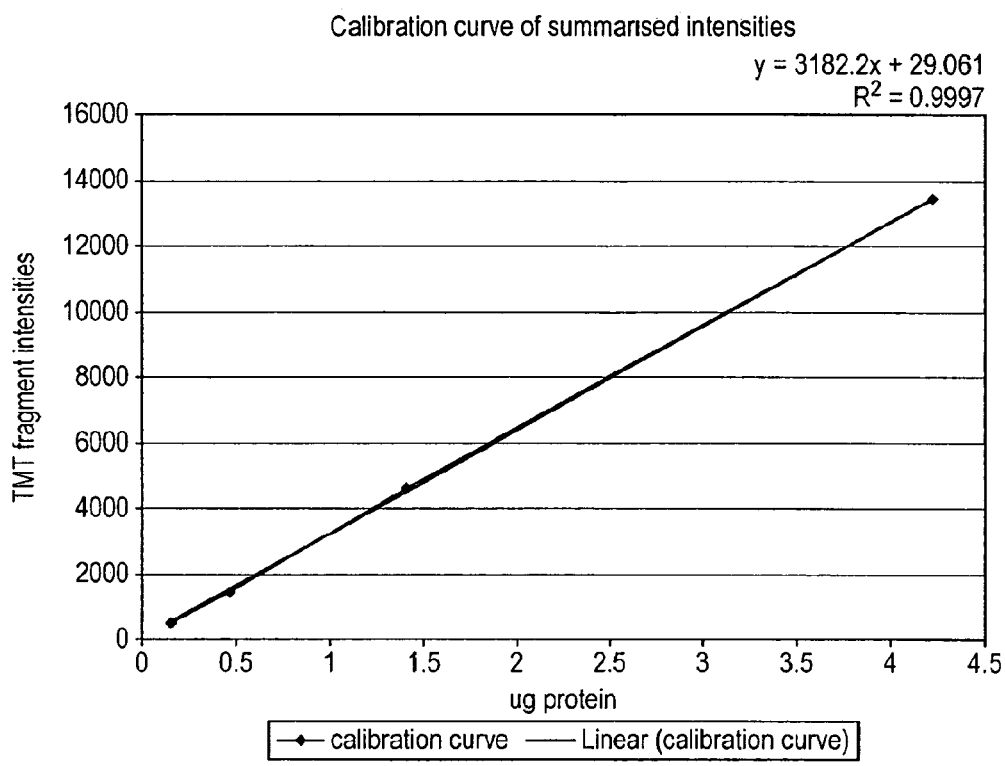
FIG. 3 shows the four point calibration curve for a set of isobarically-labelled bovine serum albumin aliquots in a calibration sample.
Figure 4:
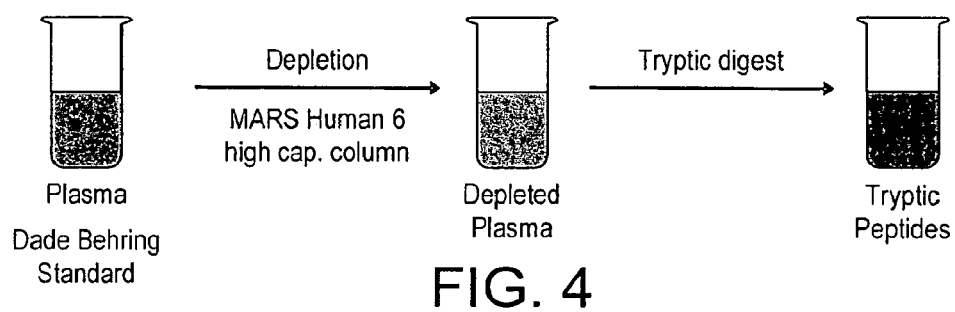
FIG. 4 shows a schematic of a method of preparing a plasma sample for use in the present invention.
Figure 5:
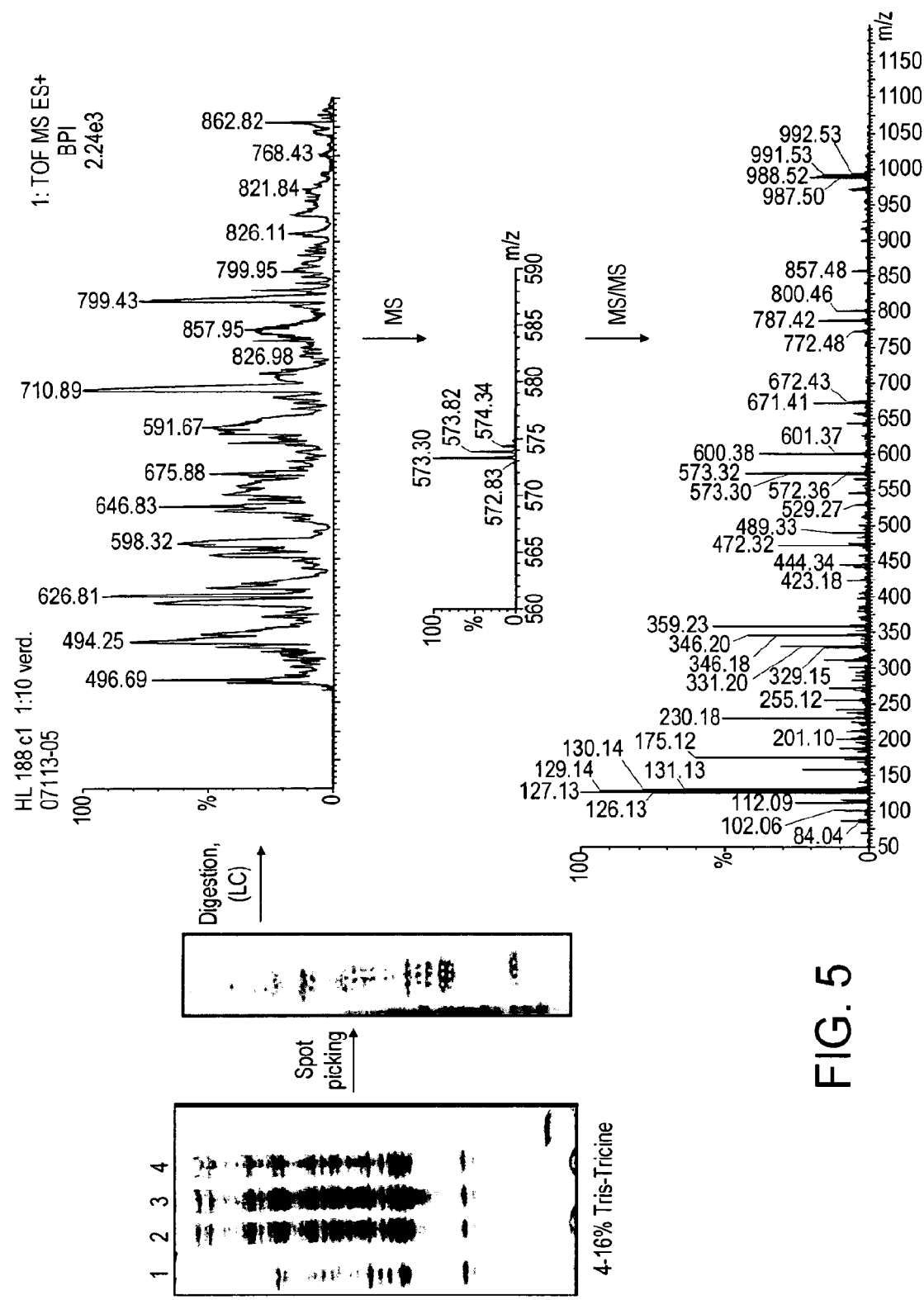
FIG. 5 shows a schematic of a method according to the present invention wherein prior to mass spectrometry analysis a mixture comprising a sample and a calibration sample is run on a 1D PAGE gel, and an appropriate spot on the gel is picked and digested.

The standard curve for this experiment was calculated by adding all the TMT mass marker moiety intensities of the BSA-derived tryptic peptides (128, 129, 130 & 131 Da respectively) for each reference amount of BSA and plotting the summed ion intensity against absolute BSA amount injected. The standard curve is shown in FIG. 3. To calculate the amount of BSA in the analytical sample the ion intensities of all of the 126 Da TMT mass marker moiety intensities were added and this value read against the standard curve. This gave a calculated BSA amount injected of 0.892 µg (one outlier peptide discarded for analysis). If data for individual peptides were used the calculated range was 0.751 to 1.016 µg BSA.

TABLE 2

Relative ion intensity, slope characteristics and calculation of absolute peptide amount in test sample - four-point reference of BSA

| BSA peptide Sequence | Peak retention time | | Sample ion intensity | Reference ion intensity | | | | Slope characteristics (y = mx + b) | | | Absolute peptide concentration (Actual input 1 µg) |
|---|---|---|---|---|---|---|---|---|---|---|---|
| | (min) | | 126 | 128 | 129 | 130 | 131 | | | | |
| | start | end | Da | Da | Da | Da | Da | m | b | r2 | (µg) |
| K.A]EFVEVTK.L | 36.16 | 36.16 | 489.39 | 84.34 | 225.73 | 690.79 | 1971.28 | 464.4 | 17.3 | 1.000 | 1.016 |
| K.A]FDEK.L | 28.66 | 28.66 | 222.49 | 46.29 | 101.51 | 396.07 | 1079.19 | 256.3 | 5.3 | 0.998 | 0.847 |
| K.A]WSVAR.L | 30.11 | 30.11 | 807.32 | 142.32 | 354.13 | 1285.76 | 3567.41 | 847.2 | 13.7 | 0.999 | 0.937 |
| K.K]VPQVSTPTLVEVSR.N | 35.92 | 35.92 | 29.43 | 14.26 | 45.00 | 148.96 | 421.26 | 100.1 | 1.0 | 0.999 | 0.284 |
| K.L]GEYGFQNALIVR.Y | 49.69 | 49.69 | 14.22 | 0.00 | 8.16 | 23.76 | 64.49 | — | — | — | — |
| K.L]GEYGFQNALIVR.Y | 53.12 | 53.12 | 2.10 | 0.00 | 0.00 | 0.00 | 19.12 | — | — | — | — |

TABLE 2-continued

Relative ion intensity, slope characteristics and calculation of absolute peptide amount in test sample - four-point reference of BSA

| | Peak retention time | | Sample ion intensity | Reference ion intensity | | | | Slope characteristics | | | Absolute peptide concentration (Actual |
|---|---|---|---|---|---|---|---|---|---|---|---|
| | (min) | | 126 | 128 | 129 | 130 | 131 | (y = mx + b) | | | input 1 µg) |
| BSA peptide Sequence | start | end | Da | Da | Da | Da | Da | m | b | r2 | (µg) |
| K.L]VNELTEFAK.T | 52.92 | 52.92 | 19.45 | 0.00 | 5.11 | 34.80 | 103.88 | — | — | — | — |
| K.L]VTDLTK.V | 39.48 | 39.48 | 410.41 | 77.59 | 241.53 | 715.05 | 2075.43 | 490.3 | 11.3 | 1.000 | 0.814 |
| K.Q]NCDQFEK.L | 26.67 | 26.67 | 214.62 | 31.42 | 112.63 | 285.43 | 1013.20 | 241.8 | −17.1 | 0.997 | 0.958 |
| K.Q]TALVELLK.H | 50.03 | 50.03 | 144.95 | 29.74 | 77.77 | 288.61 | 810.59 | 193.2 | −0.2 | 0.999 | 0.751 |
| K.Q]TALVELLK.H | 51.63 | 51.63 | 12.19 | 0.00 | 0.00 | 29.65 | 87.27 | — | — | — | — |
| K.V]LTSSAR.Q | 23.30 | 23.30 | 259.29 | 57.48 | 154.79 | 412.19 | 1249.77 | 293.1 | 10.7 | 1.000 | 0.848 |
| K.Y]LYEIAR.R | 40.62 | 40.62 | 221.01 | 31.09 | 101.50 | 332.90 | 955.92 | 227.5 | −0.0 | 1.000 | 0.972 |

Example 3. Analysis of a Plasma Sample to Detect a Specific Protein Biomarker Candidate 10 crude human plasma samples were used.

The analyte of interest to be quantified by using the invention was the protein clusterin. One clusterin peptide with the amino acid sequence depicted below was used as a reference:

VTTVASHTSDSDVPSGVTEVVVK

This peptide has a molecular weight of 2313.17 Da (monoisotopic) or 2314.53 Da (average). This peptide corresponds to residues 386-408 within the SwissProt entry (CLUS_HUMAN), and is a part of the a chain of matured clusterin that has a molecular weight of 25878 Da. The peptide is estimated to contain 3× TFA counter ions, causing an increase of the molecular weight to 2655 g/mol when generating the peptide stock.

Generation of the Calibration Sample from the Peptide

Figure 6:
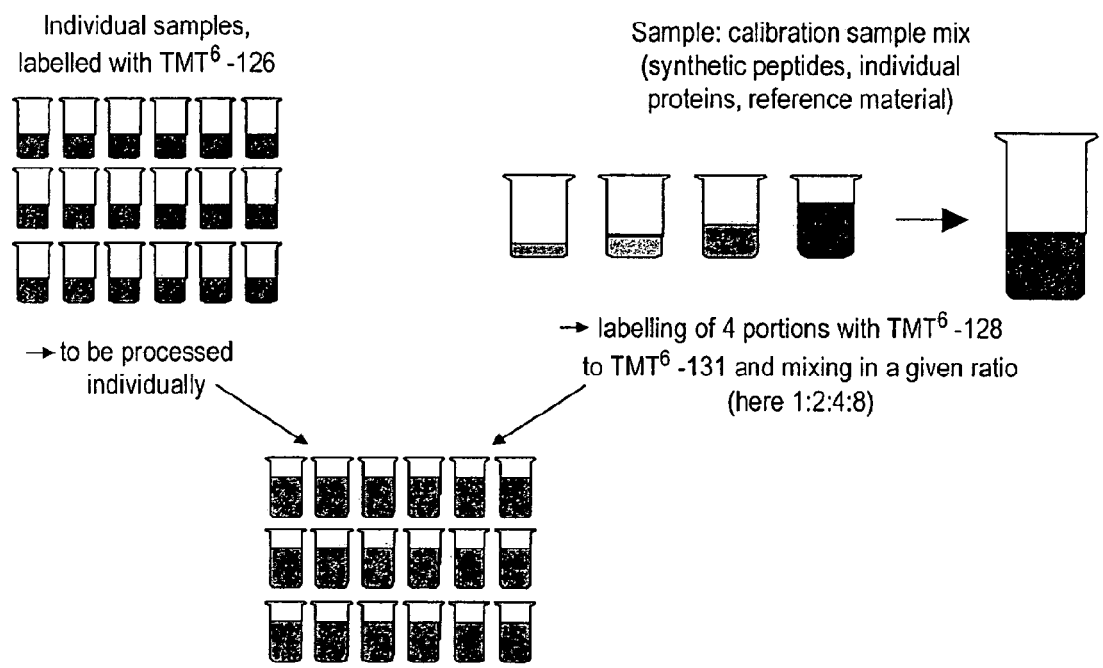
FIG. 6 shows a schematic of a method according to the present invention for assaying an analyte in a plurality of samples.

A 1 µg/µL peptide stock was obtained from 1.66 mg peptide. 4 portions of 200 µL each were labelled with TMT6-128, TMT6-129, TMT6-130 and TMT6-131 respectively. The peptides were treated with NH$_2$OH to reverse possible Tyrosine, Serine and Threonine labelling. The differentially labelled peptide samples were then mixed in a 1:2:4:8 ratio. FIG. 6 shows a schematic of the methodology used. Initial analysis by LC-MS/MS showed that partial overlabelling was not completely reversed, and therefore a second treatment was necessary. The calibration sample was diluted by a factor of 528 prior to mixing with the TMT6-128 labelled plasma samples.

Processing of the Plasma Samples 10 plasma samples were from chosen a cohort based on their clusterin content as determined by ELISA. 1.66 µL of each plasma sample was diluted with 198.33 µL buffer (100 mM TEAB, 0.1% SDS, pH 8.5), providing 142-200 µg protein in total (0.71-1.00 µg/µL protein concentration). Each plasma sample was then labeled with TMT6-126, and an NH$_2$OH treatment was carried out according to the optimised conditions. 4 µL of diluted calibration sample was then added to 10% of each sample. The sample was then purified by reverse phase as well as strong cation exchange chromatography.

LC-MS/MS

LC-MS/MS was carried out using a CapLC coupled to a Qtof-2 ® mass spectrometer (Waters, Manchester, UK)

Figure 7:
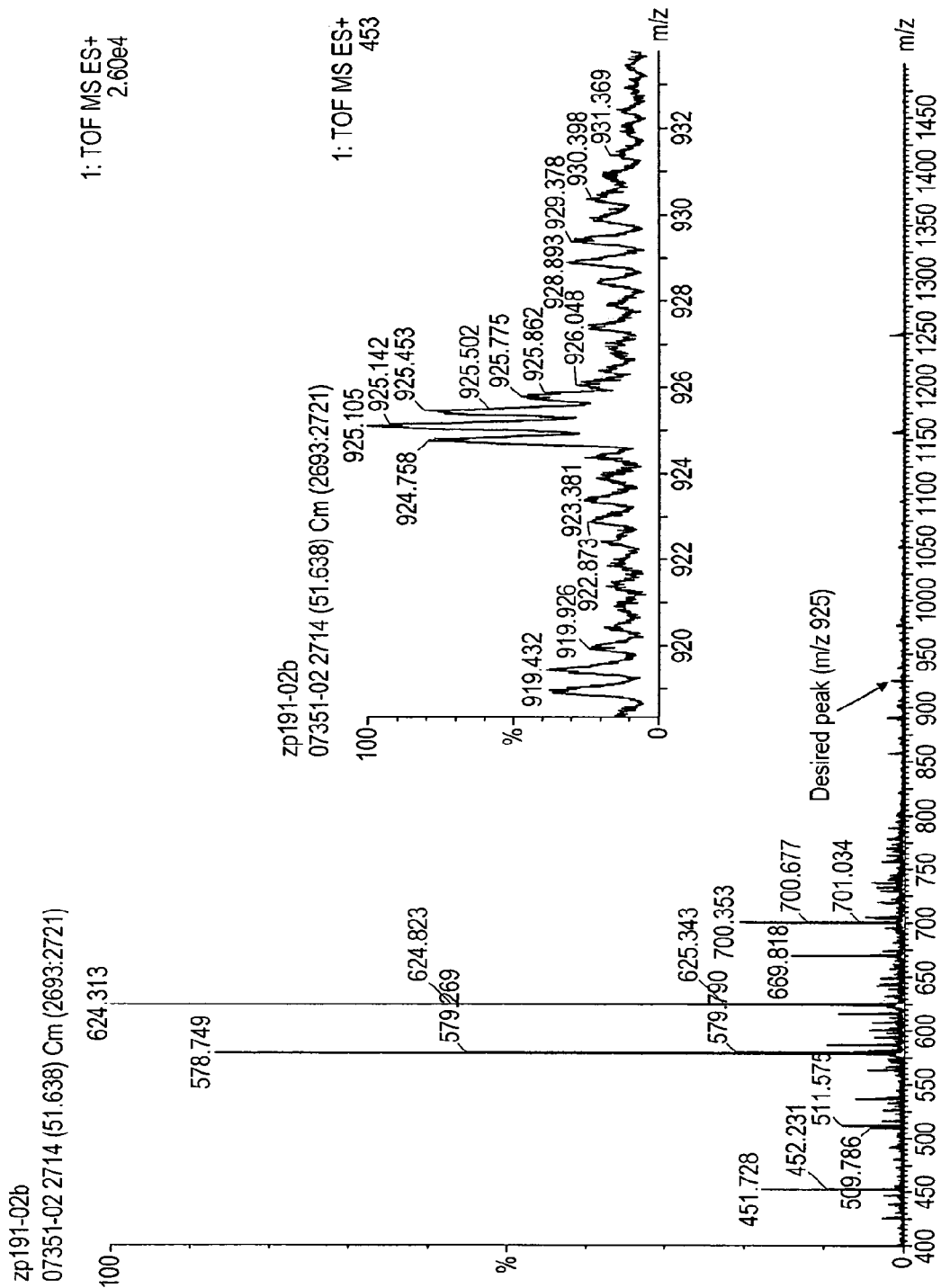
FIG. 7 shows an accumulated MS from the retention profile of a labelled peptide from clusterin as described in Example 3 below. Inset—zoom view of m/z region 915-935 showing the peptide of interest.
Figure 8:
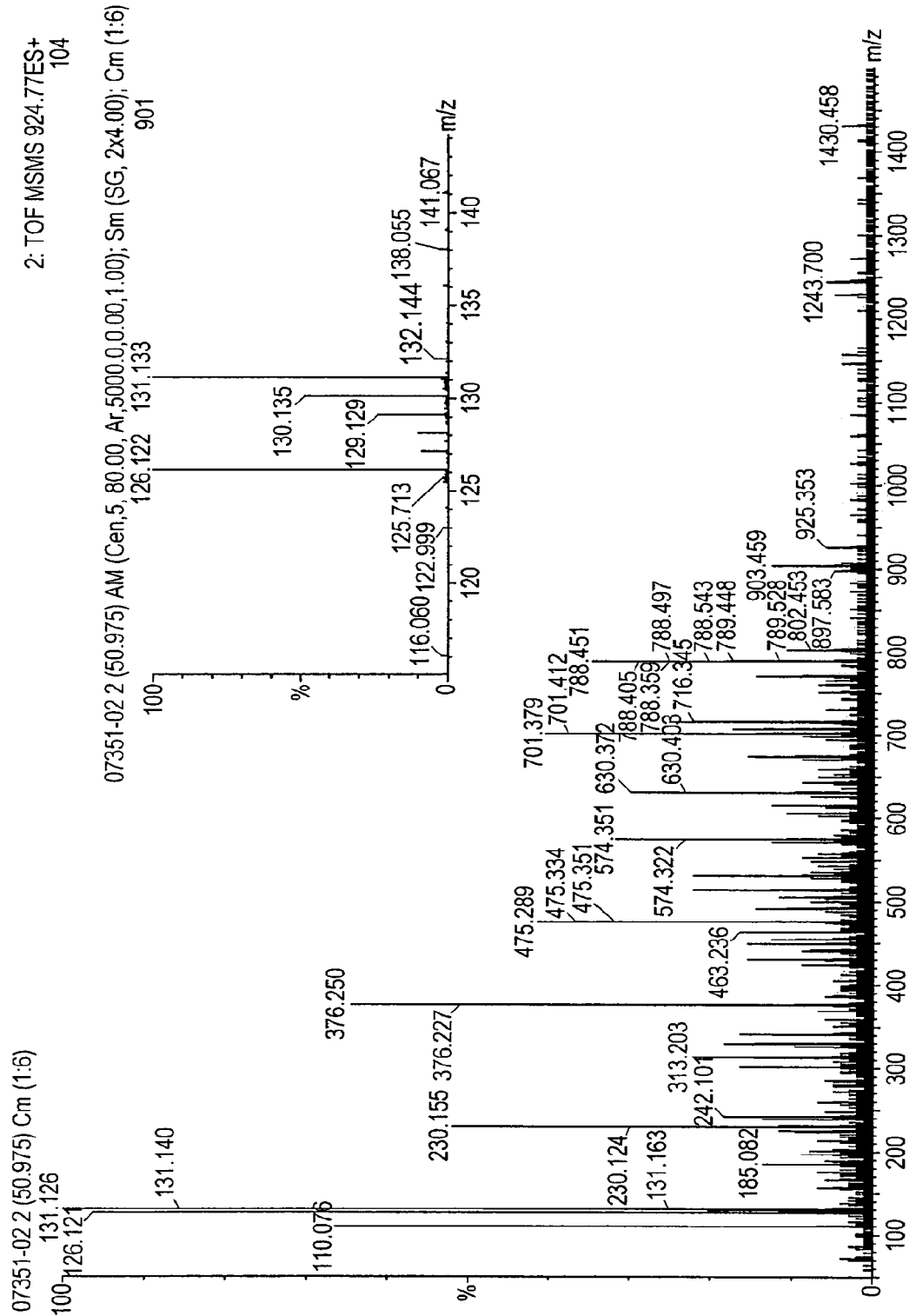
FIG. 8 shows an accumulated MS/MS spectrum of the labelled peptide from clusterin. Insert: Zoom view at the mass marker region.

5 µl of purified sample was injected per run (corresponding to 40 nL crude plasma). FIG. 7 shows the mass spectrum from the retention profile of the labelled peptide from clusterin. Targeted MS/MS acquisition was then carried out using include lists that contained the m/z of the TMT-labelled peptide from clusterin. Optimisation of collision energy parameters was performed to obtain increased mass marker group ion intensities. FIG. 8 shows the MS/MS spectrum of the labelled peptide from clusterin. As inset is shown the region of the MS/MS spectrum which shows the mass marker ions.

Data Analysis

Figure 9:
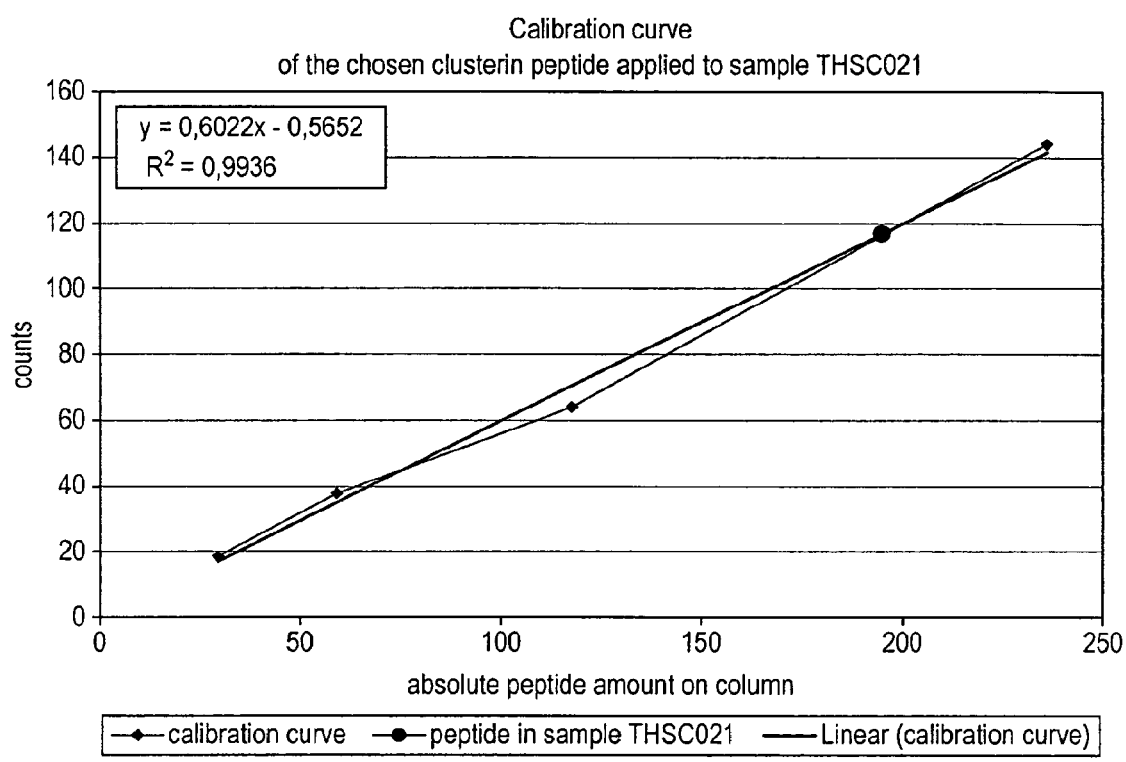
FIG. 9 shows a calibration curve of the chosen clusterin peptide.

Manual accumulation of all corresponding MS/MS scans was performed to obtain 1 MS/MS file per run. Peak processing and ID was then performed using standard methodologies. A calibration curve was generated for each MS/MS file based on the mass marker ion intensities 128-131 (linear regression) (FIG. 9). The amount of peptide present in each sample was then determined using the calibration curve (Table 3). Finally, the clusterin concentration per sample in µg/mL was calculated based on the molecular weight of clusterin α chain.

TABLE 3

| Sample ID | Experimental code | R square of the calibration curve | calculated amount of peptide from plasma sample on column (fmol) | concentration of peptide in plasma samples (nmol/mL) | concentration of Clusterin in plasma samples (µg/mL)* |
|---|---|---|---|---|---|
| PRG042 | ZP191-1 | 0.996 | 291 | 7.0 | 182 |
| TLS712 | ZP191-2 | 1.000 | 236 | 5.7 | 148 |
| LNDO137 | ZP191-3 | 0.995 | 247 | 6.0 | 155 |
| THSA046 | ZP191-4 | 0.997 | 180 | 4.4 | 113 |
| THSA034 | ZP191-5 | 0.999 | 199 | 4.8 | 125 |
| THSM044 | ZP191-6 | 0.986 | 208 | 5.0 | 130 |

TABLE 3-continued

| Sample ID | Experimental code | R square of the calibration curve | calculated amount of peptide from plasma sample on column (fmol) | concentration of peptide in plasma samples (nmol/mL) | concentration of Clusterin in plasma samples (µg/mL)* |
|---|---|---|---|---|---|
| THSC021 | ZP191-7 | 0.994 | 195 | 4.7 | 122 |
| LDZC004 | ZP191-8 | 0.995 | 197 | 4.8 | 124 |
| THSA023 | ZP191-9 | 0.987 | 327 | 7.9 | 205 |
| K708A | ZP191-10 | 0.995 | 178 | 4.3 | 111 |

Example 4. Preparation of a Whole Proteome Qualitative Reference Standard

In many circumstances, for example in early_biomarker discovery workflows, it is not essential to have absolute quantitative reference standards but rather a representative and uniform standard covering the whole proteome to be analysed in which the absolute quantity of any given analyte is unknown but is deemed to be in the normal range of the reference sample. One example of such a whole proteome standard is human plasma. Using the present invention it is possible to prepare a universal and uniform reference standard plasma in which all proteins and/or peptides are present as isobarically labelled multiple qualitative standards. When such a standard is added to an analytical sample wherein all proteins and/or peptides have been labelled with a different member of the same set of isobaric labels it is possible to perform quantitative MS/MS assays on all precursor ions detected in MS and to determine the relative abundance of the analyte in the analytical sample compared to the reference standard.

The skilled addressee would well understand that this concept can be applied to any qualitative standard including but not limited to whole or depleted plasma, serum, cerebro spinal fluid, synovial fluid, urine, semen, nipple aspirate, tissue homogenate, cell culture supernatant, cell extracts, sub-cellular fractions, membrane preparations etc. and that individual reference materials representing a specific sample type may be prepared for example to normalise biomarker studies across multi-centre clinical trials.

As an example of such a reference material preparation of a human reference plasma was performed. Using 4 different isobaric mass tags, plasma was labeled and mixed to create a whole plasma proteome calibration mixture. After chromatographic separation by 1. Strong cation exchanger (SCX) into 24 fractions and 2. Reversed-phase HPLC into 480 spots on a stainless steel MALDI-target. Spots were subsequently analysed by MS and MS/MS in a 4800 MALDI Tof/Tof mass spectrometer (Applied Biosystems, USA).

Materials and Methods

Human Plasma was purchased from Dade Behring (Standard Plasma). The plasma was spiked with two proteins:
1) Ribonuclease A Type I-AS: From Bovine Pancreas (Sigma, R-5503), MW 13.7 kDa; pI 9.6; 85% purity. 1.8 mg were dissolved in 170 µL water; 10 µL of this solution was added to 1 ml Plasma prior to depletion of high abundant proteins.
2) Trypsin Inhibitor, Type I-S: From Soybean (Sigma, T-9003); MW 20.1 kDa; pI 4.5; 90% Protein content; α-chain MW 20090 Da; β-Chain MW 20036 Da; γ-Chain MW 20163 Da. 8.8 mg were dissolved in 196 µL water; 10 µL of this solution was added to 1 ml Plasma prior to depletion of high abundant proteins.

Prior to isobaric mass labeling six high abundant proteins (human albumin, IgG, Antitrypsin, IgA, transferrin and haptoglobin) were depleted using an Agilent high capacity MARS 4.6×100 mm Column (Part-Nr. 518-5333) on a BioCAD Vision HPLC from Applied Biosystems Reduction, Alkylation and Digest with Trypsin The Protein treatment was performed following standard protocols. Protein was diluted to a 1 g/L protein solution pH 7.5 in 100 mM Borate buffer and 0.1% Sodium dodecylsulfate. Reduction of the cysteins with 1 mM TCEP was performed for 30 min at room temperature. The cysteins were alkylated with Iodoacetamide for one hour at room temperature. 440 µg Trypsin were added and incubated for 18-24 hours at 37° C.

Assembling of a 1:2:4:8 Proportion and Labelling with TMT[6]

After tryptic digestion depleted plasma was split into four aliquots that were independently labelled with the different isobaric label TMTsixplex reagents TMT[6]-128, TMT[6]-129, TMT[6]-130 and TMT[6]-131. After labeling the aliquots were mixed volumetrically in the ratio 1:2:4:8 respectively to generate a plasma 4-point calibration mixture (FIG. 1). To determine the proteome coverage of the reference material it was subjected to multi-dimensional chromatography and tandem mass spectrometry analysis Collection of 24 Strong Cation Exchange Fractions Prior to mass spectrometry a first separation was performed on a BioCAD Vision HPLC from Applied Biosystems on a SCX column (Poly LC 4.6 i.d.×100 mm; Polysulfoethyl A). The sample was trapped on a Waters Sunfire RP PreColumn (4.0 mm i.d.×10 mm), and eluted with a 50% Acetonitrile pulse to the SCX column. The PreColumn was switched offline when the elution gradient for the SCX started. The SCX gradient was formed with solvents C (Water 75% Acetonitrile 25%+5 mM $KH_2PO_4$, pH 3) and D (Water 75% Acetonitrile 25%+5 mM $KH_2PO_4$, pH 3+500 mM KCl, pH 3) from 0 to 50% in 30 minutes. 24 SCX fractions were collected from this separation step. Each fraction was subsequently subjected to reverse-phase separation.

Reversed Phase HPLC

The second separation system was a reversed phase chromatography on a Waters nanoAQUITY UPLC System. Due to the decoupling of the chromatography and the MS measurements in the MALDI workflow the HPLC conditions could be optimized to get a high peak capacity. Column: 75 µm I.D.×250 mm filled with 1.7 µm BEH 130 C18 packing material (Waters part Nr.: 186003545). Column oven temperature 60° C. 5 µL of each SCX fraction were injected directly without any precolumn on the UPLC column.

Gradient:

TABLE 4

| Time(min) | % Acetonitrile |
|---|---|
| 1. Initial | 5 |
| 2. 31.00 | 5 |
| 3. 150.00 | 25 |
| 4. 210.00 | 50 |
| 5. 220.00 | 95 |
| 6. 225.00 | 95 |
| 7. 226.00 | 5 |

MALDI Target Spotting

The separation column of the nanoACQUITY UPLC System is joined to the inlet of a Dionex Probot spotter to fractionate the peptides in MALDI preparations on a Microtiter format MALDI sample target for the 4800 Tof/Tof MALDI instrument. On a MALDI target 1920 individual fractions can be collected. Four RP chromatograms each with 480 spots were prepared per MALDI target. The spotting starts at retention time 50 minutes and ends at retention time 210 min with a spotting duration of 20 seconds per spot. On the spotter the eluent flow of 0.35 µL per minute is mixed with a MALDI matrix solution (5 g/L solution of α-cyan-4-Hydroxycinnamic acid in 80% Acetonitrile, 19.8% water, 0.2% Trifluoracetic acid) flow of 0.6 µL per minute. Each MALDI preparation has a volume of about 330 nL.

MALDI MS and MS/MS Analysis on the 4800 Tof/Tof Instrument

The spots were run in two modes on the 4800 Tof/Tof instrument. In a first run in Reflector mode conventional MS spectra were recorded. 1,000 MALDI Shots were summed up for each individual MS Spectrum. The spectra were calibrated internally with the matrix trimer signal at m/z 568.138 Th. The interpretation tool of the "4000 Series Explorer" instrument software generated a precursor list of MS/MS experiments using a LC MALDI strategy that includes the calculation of elution profiles for the peptide peaks (fraction to fraction mass tolerance 100 ppm, exclusion of precursors within 200 resolution). Up to five precursors were allowed per spot to be selected for subsequent MS/MS analysis. The MS/MS acquisition was on the strongest precursors first. 1,000 laser shots were acquired per spectrum. The MS/MS spectra were calibrated internally with the theoretical mass value of the $TMT^6$-131 fragment ion 131.1387 Th.

MASCOT Data Base Search for Identification

Data base search with 15818 queries was performed with MASCOT Version 2.1.04. Human proteins were identified in a search with the IPI Human Data base (IPI_Human_20071024; 68348 sequences; 28969400 residues). Both spiked proteins were not present in the IPI Human data base; they were searched in the Swissprot database using the taxonomy key "Other mammalia". The peak areas of the masses 126, 127, 128, 129, 130, 131 were extracted from the TOFTOF Matcher from the Sequest Toolbox.

Results
Quantitative Analysis

The Quantitation of reporter peaks at the masses 128, 129, 130 and 131 Da was performed via the Extraction of the Peak areas out of the GPS Oracle data base. After peak area calculation, regression analysis was performed in order to check for quality of the calibration curve (1:2:4:8 ratio). Each peptide MS/MS experiment was checked by analysing the reporter peaks for the fit to a straight line. A linear regression was performed for every MS/MS spectrum.

Figure 10:
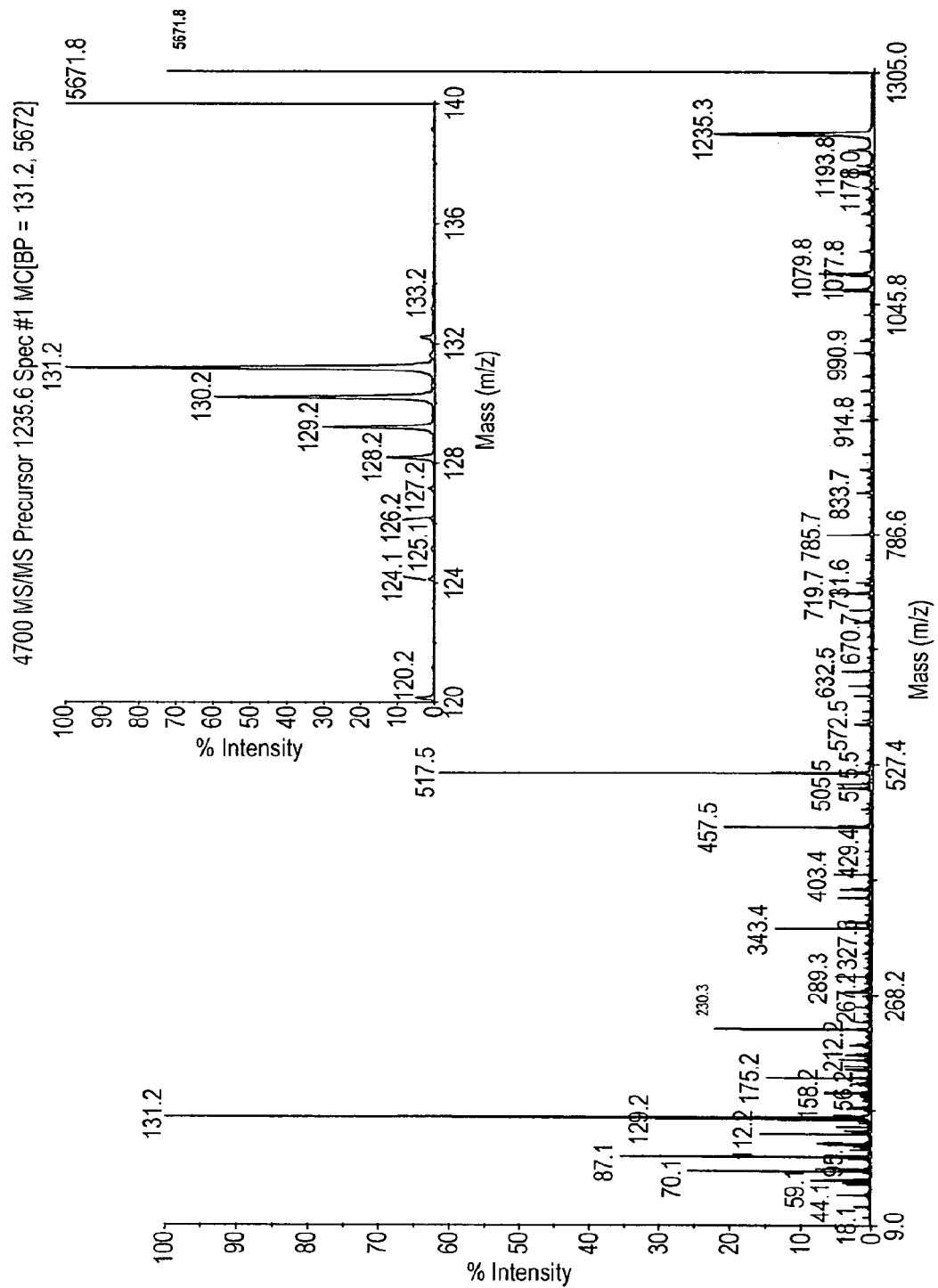
FIG. 10 shows a MALDI MS/MS spectrum of peptide FQVDNNNR (SEQ ID NO: 1) as described in Example 4 below.
Figure 11:
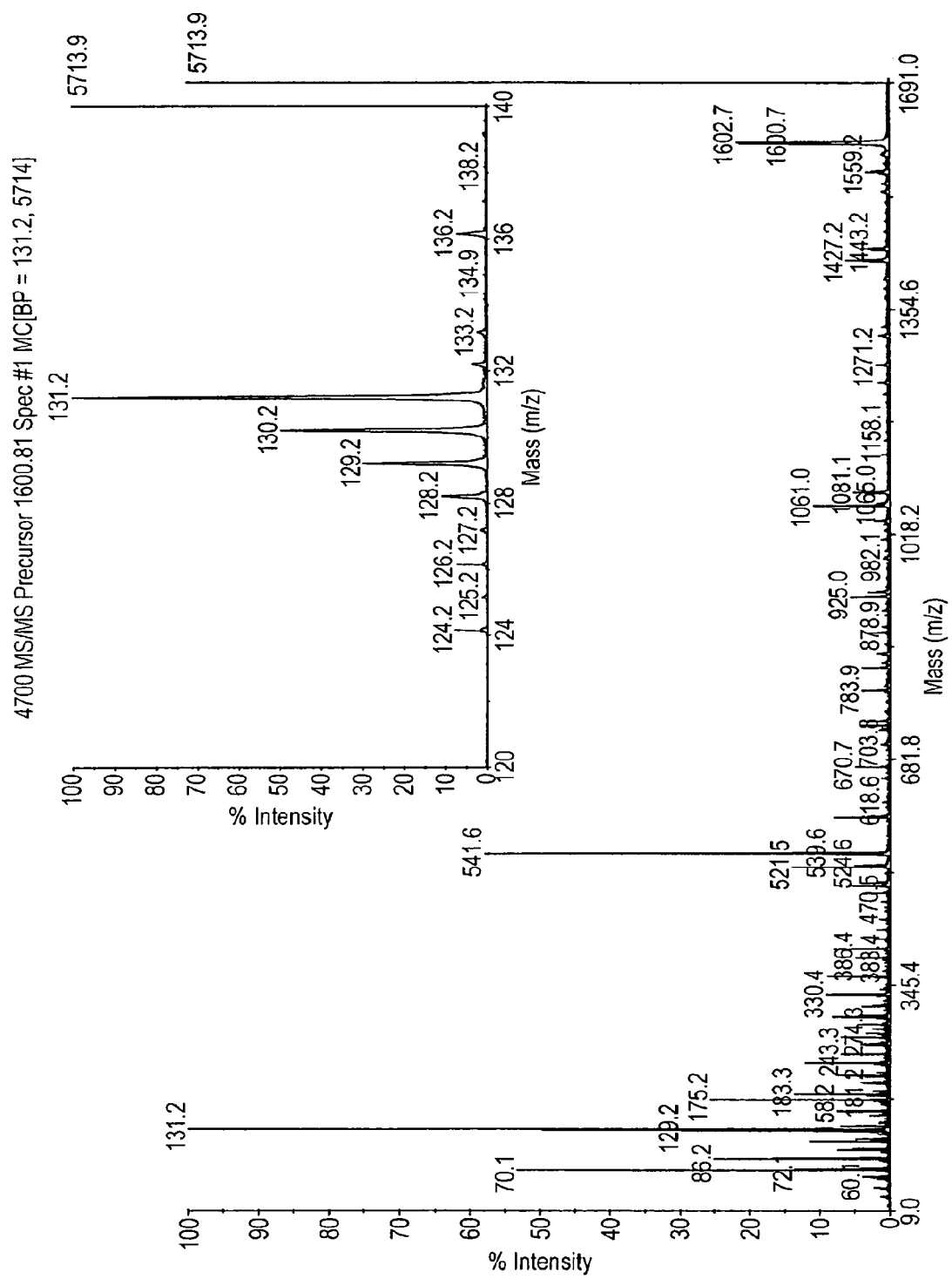
FIG. 11 shows a MALDI MS/MS spectrum of peptide GAYPLSIEPIGVR (SEQ ID NO: 2) as described in Example 4 below.
Figure 12:
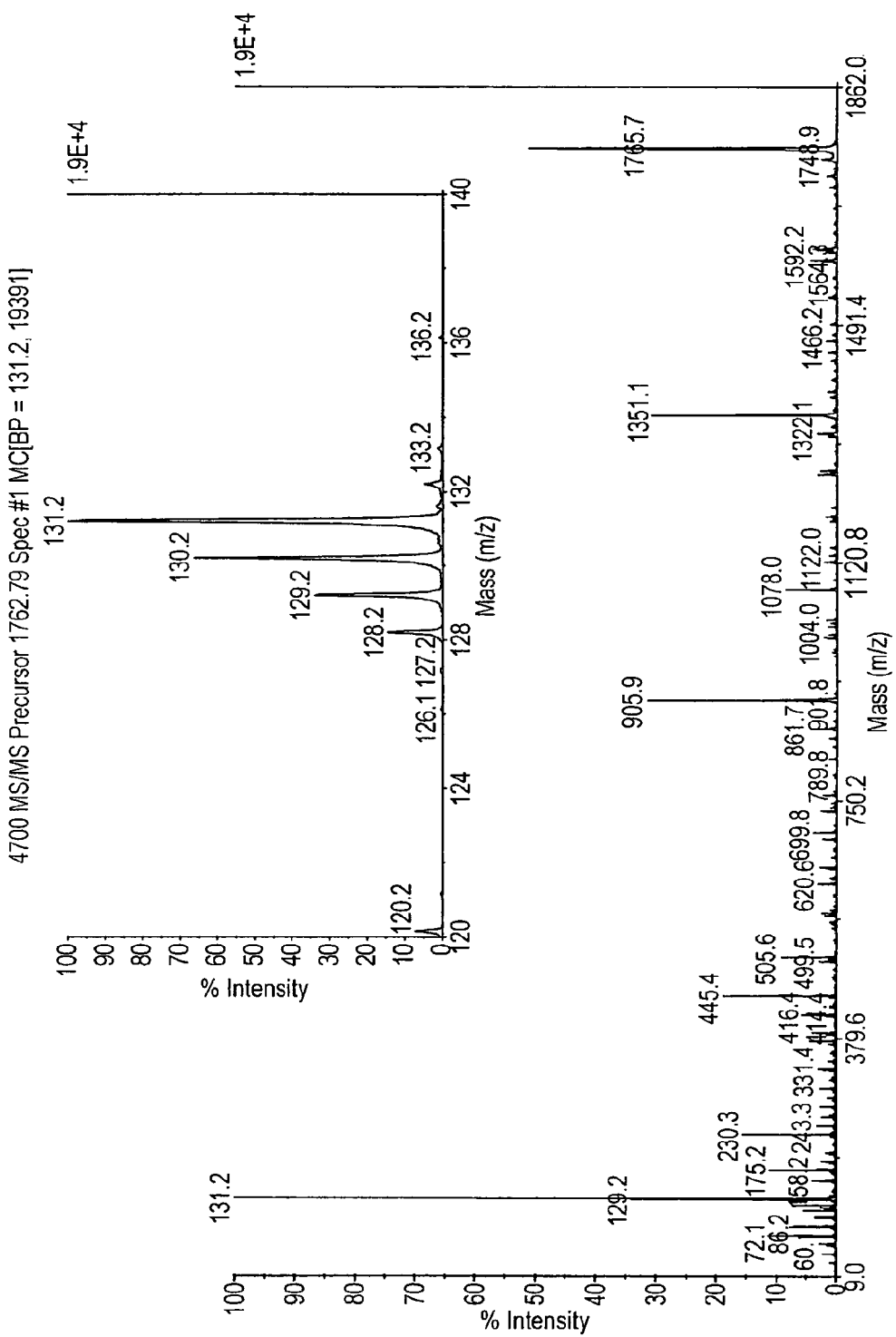
FIG. 12 shows a MALDI MS/MS spectrum of peptide GQYCYELDEK (SEQ ID NO: 3) as described in Example 4 below.

FIGS. 10, 11 and 12 show representative examples of an MS/MS spectrum. In the expanded view, the sequencing b- and y-ions are seen. In the insert a zoom is displayed demonstrating the reporter region with the reporters on 128, 129, 130 and 131 m/z with their 1:2:4:8 ratios.

The regression analysis showed that 12,000 MS/MS spectra fulfil certain $R^2$ values (see Table 5):

TABLE 5

$R^2$ value distribution of 12,000 MS/MS spectra from TMT-4-point calibration plasma.

| $R^2$ | Nr of MS/MS | in % |
|---|---|---|
| 0.999 | 2368 | 17.0 |
| 0.995 | 6439 | 46.1 |
| 0.99 | 8589 | 61.6 |
| 0.98 | 10439 | 74.8 |
| 0.97 | 11361 | 81.4 |
| 0.96 | 11926 | 85.5 |
| 0.95 | 12308 | 88.2 |
| 0.94 | 12571 | 90.1 |
| 0.93 | 12805 | 91.8 |
| 0.92 | 12970 | 93.0 |
| 0.91 | 13124 | 94.1 |
| 0.9 | 13247 | 94.9 |
| 0.7 | 13835 | 99.2 |
| 0.6 | 13875 | 99.4 |
| 0.5 | 13904 | 99.6 |

Summary

In total, about 12,000 MS/MS spectra were generated which showed reporter ion intensities fulfilling the intensity criteria for quantification. The MALDI TofTof MS/MS spectra show the TMT tag fragment ion in good intensity to allow for quantification purposes. The y- and b-ion series in the MS/MS spectra of the peptides were used for peptide ID. The data base search with conservative thresholds gave 141 human protein identifications in the IPI Human data base. Both spiked proteins were found using the Swissprot database and species related filtering. Among the identified human proteins there was for example Clusterin found with 18 MS/MS spectra and 25% Sequence coverage. Regression analysis shows that more than half of the MS/MS spectra have a $R^2$ value better than 0.99. 90% have a $R^2$ value better than 0.94.

In addition to the spiked proteins, 141 human proteins were identified when a minimal peptide score threshold of 20 was applied and a protein threshold greater than 45 (Table 6).

TABLE 6

Database: IPI_human 20071024 (68348 sequences; 28969400 residues)
Significant hits:

| | | |
|---|---|---|
| 1. | IPI00164623 | Gene_Symbol = C3 187 kDa protein |
| 2. | IPI00478003 | Gene_Symbol = A2M Alpha-2-macroglobulin precursor |
| 3. | IPI00022229 | Gene_Symbol = APOB Apolipoprotein B-100 precursor |

TABLE 6-continued

Database: IPI_human 20071024 (68348 sequences; 28969400 residues)
Significant hits:

4. IPI00021885 Gene_Symbol = FGA Isoform 1 of Fibrinogen alpha chain precursor
5. IPI00298497 Gene_Symbol = FGB Fibrinogen beta chain precursor
6. IPI00414283 Gene_Symbol = FN1 fibronectin 1 isoform 4 preproprotein
7. IPI00418163 Gene_Symbol = C4B; C4A C4B1
8. IPI00215894 Gene_Symbol = KNG1 Isoform LMW of Kininogen-1 precursor
9. IPI00017601 Gene_Symbol = CP Ceruloplasmin precursor
10. IPI00032328 Gene_Symbol = KNG1 Isoform HMW of Kininogen-1 precursor
11. IPI00305461 Gene_Symbol = ITIH2 Inter-alpha-trypsin inhibitor heavy chain H2 precursor
12. IPI00021891 Gene_Symbol = FGG Isoform Gamma-B of Fibrinogen gamma chain precursor
13. IPI00021841 Gene_Symbol = APOA1 Apolipoprotein A-I precursor
14. IPI00292530 Gene_Symbol = ITIH1 Inter-alpha-trypsin inhibitor heavy chain H1 precursor
15. IPI00029739 Gene_Symbol = CFH Isoform 1 of Complement factor H precursor
16. IPI00218192 Gene_Symbol = ITIH4 Isoform 2 of Inter-alpha-trypsin inhibitor heavy chain H4 precursor
17. IPI00550991 Gene Symbol = SERPINA3 Alpha-1-antichymotrypsin precursor
18. IPI00019591 Gene_Symbol = CFB Isoform 1 of Complement factor B precursor (Fragment)
19. IPI00294193 Gene_Symbol = ITIH4; TMEM110 Isoform 1 of Inter-alpha-trypsin inhibitor heavy chain H4 precursor
20. IPI00026314 Gene_Symbol = GSN Isoform 1 of Gelsolin precursor
21. IPI00022895 Gene_Symbol = A1BG Alpha-1B-glycoprotein precursor
22. IPI00793618 Gene_Symbol = C3 13 kDa protein
23. IPI00022488 Gene_Symbol = HPX Hemopexin precursor
24. IPI00641737 Gene_Symbol = HP Haptoglobin precursor
25. IPI00022391 Gene_Symbol = APCS Serum amyloid P-component precursor
26. IPI00019580 Gene_Symbol = PLG Plasminogen precursor
27. IPI00298828 Gene_Symbol = APOH Beta-2-glycoprotein 1 precursor
28. IPI00019568 Gene_Symbol = F2 Prothrombin precursor (Fragment)
29. IPI00218732 Gene_Symbol = PON1 Serum paraoxonase/arylesterase 1
30. IPI00022431 Gene_Symbol = AHSG Alpha-2-HS-glycoprotein precursor
31. IPI00032291 Gene_Symbol = C5 Complement C5 precursor
32. IPI00829768 Gene_Symbol = IGHM IGHM protein
33. IPI00477090 Gene_Symbol = IGHM IGHM protein
34. IPI00844156 Gene_Symbol = SERPINC1 SERPINC1 protein
35. IPI00032179 Gene_Symbol = SERPINC1 Antithrombin III variant
36. IPI00304273 Gene_Symbol = APOA4 Apolipoprotein A-IV precursor
37. IPI00022426 Gene_Symbol = AMBP AMBP protein precursor
38. IPI00298971 Gene_Symbol = VTN Vitronectin precursor
39. IPI00025426 Gene_Symbol = PZP Pregnancy zone protein precursor
40. IPI00022371 Gene_Symbol = HRG Histidine-rich glycoprotein precursor
41. IPI00022394 Gene_Symbol = C1QC Complement C1q subcomponent subunit C precursor
42. IPI00477597 Gene_Symbol = HPR Isoform 1 of Haptoglobin-related protein precursor
43. IPI00021857 Gene_Symbol = APOC3 Apolipoprotein C-III precursor
44. IPI00555812 Gene_Symbol = GC Vitamin D-binding protein precursor
45. IPI00291262 Gene_Symbol = CLU Clusterin precursor
46. IPI00029863 Gene_Symbol = SERPINF2 Alpha-2-antiplasmin precursor
47. IPI00021842 Gene_Symbol = APOE Apolipoprotein E precursor
48. IPI00017696 Gene_Symbol = C1S Complement C1s subcomponent precursor
49. IPI00291866 Gene_Symbol = SERPING1 Plasma protease C1 inhibitor precursor
50. IPI00021727 Gene_Symbol = C4BPA C4b-binding protein alpha chain precursor
51. IPI00006114 Gene_Symbol = SERPINF1 Pigment epithelium-derived factor precursor
52. IPI00011261 Gene_Symbol = C8G Complement component C8 gamma chain precursor
53. IPI00186903 Gene_Symbol = APOL1 Isoform 2 of Apolipoprotein-L1 precursor
54. IPI00021854 Gene_Symbol = APOA2 Apolipoprotein A-II precursor
55. IPI00293925 Gene_Symbol = FCN3 Isoform 1 of Ficolin-3 precursor
56. IPI00292950 Gene_Symbol = SERPIND1 Heparin cofactor 2 precursor
57. IPI00386879 Gene_Symbol = IGHA1 CDNA FLJ14473 fis, clone MAMMA1001080, highly similar to Homo sapiens SNC73 prot
58. IPI00007221 Gene_Symbol = SERPINA5 Plasma serine protease inhibitor precursor
59. IPI00385264 Gene_Symbol =- Ig mu heavy chain disease protein
60. IPI00006662 Gene_Symbol = APOD Apolipoprotein D precursor
61. IPI00303963 Gene_Symbol = C2 Complement C2 precursor (Fragment)
62. IPI00291867 Gene_Symbol = CFI Complement factor I precursor TABLE 6-continued Database: IPI_human 20071024 (68348 sequences; 28969400 residues)
Significant hits:

63. IPI00022395 Gene_Symbol = C9 Complement component C9 precursor
64. IPI00430820 Gene_Symbol = IGKV1-5 IGKV1-5 protein
65. IPI00009920 Gene_Symbol = C6 Complement component C6 precursor
66. IPI00020996 Gene_Symbol = IGFALS Insulin-like growth factor-binding protein complex acid labile chain precursor
67. IPI00032220 Gene_Symbol = AGT Angiotensinogen precursor
68. IPI00168728 Gene_Symbol = IGHM FLJ00385 protein (Fragment)
69. IPI00019581 Gene_Symbol = F12 Coagulation factor XII precursor
70. IPI00020986 Gene_Symbol = LUM Lumican precursor
71. IPI00294395 Gene_Symbol = C8B Complement component C8 beta chain precursor
72. IPI00654888 Gene_Symbol = KLKB1 Uncharacterized protein KLKB1
73. IPI00299503 Gene_Symbol = GPLD1 Isoform 1 of Phosphatidylinositol-glycan-specific phospholipase D precursor
74. IPI00022429 Gene_Symbol = ORM1 Alpha-1-acid glycoprotein 1 precursor
75. IPI00296608 Gene_Symbol = C7 Complement component C7 precursor
76. IPI00009793 Gene_Symbol = C1RL Complement C1r-like protein
77. IPI00019943 Gene_Symbol = AFM Afamin precursor
78. IPI00022417 Gene_Symbol = LRG1 Leucine-rich alpha-2-glycoprotein precursor
79. IPI00296165 Gene_Symbol = C1R; C17orf13; LOC442122; ACYP1; RP11-114H20.1 Complement C1r subcomponent precursor
80. IPI00020091 Gene_Symbol = ORM2 Alpha-1-acid glycoprotein 2 precursor
81. IPI00328609 Gene_Symbol = SERPINA4 Kallistatin precursor
82. IPI00011264 Gene_Symbol = CFHR1 Complement factor H-related protein 1 precursor
83. IPI00179330 Gene_Symbol = UBB; UBC; RPS27A ubiquitin and ribosomal protein S27a precursor
84. IPI00011252 Gene_Symbol = C8A Complement component C8 alpha chain precursor
85. IPI00019399 Gene_Symbol = SAA4 Serum amyloid A-4 protein precursor
86. IPI00163207 Gene_Symbol = PGLYRP2 Isoform 1 of N-acetylmuramoyl-L-alanine amidase precursor
87. IPI00022420 Gene_Symbol = RBP4 Plasma retinol-binding protein precursor
88. IPI00791350 Gene_Symbol = CLEC3B 11 kDa protein
89. IPI00218413 Gene_Symbol = BTD biotinidase precursor
90. IPI00294004 Gene_Symbol = PROS1 Vitamin K-dependent protein S precursor
91. IPI00009028 Gene_Symbol = CLEC3B Tetranectin precursor
92. IPI00382480 Gene_Symbol =- Ig heavy chain V-III region BRO
93. IPI00296176 Gene_Symbol = F9 Coagulation factor IX precursor
94. IPI00477992 Gene_Symbol = C1QB complement component 1, q subcomponent, B chain precursor
95. IPI00154742 Gene_Symbol = IGL@ IGL@ protein
96. IPI00292946 Gene_Symbol = SERPINA7 Thyroxine-binding globulin precursor
97. IPI00382938 Gene_Symbol = IGLV4-3 IGLV4-3 protein
98. IPI00299778 Gene_Symbol = PON3 Serum paraoxonase/lactonase 3
99. IPI00410714 Gene_Symbol = HBA2; HBA1 Hemoglobin subunit alpha
100. IPI00296534 Gene_Symbol = FBLN1 Isoform D of Fibulin-1 precursor
101. IPI00027235 Gene_Symbol = ATRN Isoform 1 of Attractin precursor
102. IPI00029193 Gene_Symbol = HGFAC Hepatocyte growth factor activator precursor
103. IPI00807428 Gene_Symbol =- Putative uncharacterized protein
104. IPI00022463 Gene_Symbol = TF Serotransferrin precursor
105. IPI00019576 Gene_Symbol = F10 Coagulation factor X precursor
106. IPI00794397 Gene_Symbol = CHMP4A chromatin modifying protein 4A
107. IPI00022733 Gene_Symbol = PLTP 45 kDa protein
108. IPI00024825 Gene_Symbol = PRG4 Isoform A of Proteoglycan-4 precursor
109. IPI00216882 Gene_Symbol = MASP1 mannan-binding lectin serine protease 1 isoform 3
110. IPI00387115 Gene_Symbol =- Ig kappa chain V-III region SIE
111. 1PI00003590 Gene_Symbol = QSOX1 Isoform 1 of Sulfhydryl oxidase 1 precursor
112. IPI00022432 Gene_Symbol = TTR Transthyretin precursor
113. IPI00029061 Gene_Symbol = SEPP1 Selenoprotein P precursor
114. IPI00028413 Gene_Symbol = ITIH3 Inter-alpha-trypsin inhibitor heavy chain H3 precursor
115. IPI00479116 Gene_Symbol = CPN2 Carboxypeptidase N subunit 2 precursor
116. IPI00178926 Gene_Symbol = IGJ immunoglobulin J chain
117. IPI00166729 Gene_Symbol = AZGP1 alpha-2-glycoprotein 1, zinc
118. IPI00445707 Gene_Symbol = MAEA CDNA FLJ43512 fis, clone PERIC2004028, moderately similar to *Mus musculus* erythroblast macrophage protein EMP mRNA
119. IPI00329775 Gene_Symbol = CPB2 Isoform 1 of Carboxypeptidase B2 precursor

TABLE 6-continued

Database: IPI_human 20071024 (68348 sequences; 28969400 residues)
Significant hits:

| | |
|---|---|
| 120. | IPI00008603 Gene_Symbol = ACTA2 Actin, aortic smooth muscle |
| 121. | IPI00384938 Gene_Symbol = IGHG1 Putative uncharacterized protein DKFZp686N02209 |
| 122. | IPI00784822 Gene_Symbol = IGHV4-31 IGHV4-31 protein |
| 123. | IPI00027482 Gene_Symbol = SERPINA6 Corticosteroid-binding globulin precursor |
| 124. | 1PI00795068 Gene_Symbol = RRBP1 Ribosome binding protein 1 homolog 180 kDa |
| 125. | IPI00025204 Gene_Symbol = CD5L CD5 antigen-like precursor |
| 126. | IPI00003351 Gene_Symbol = ECM1 Extracellular matrix protein 1 precursor |
| 127. | IPI00163446 Gene_Symbol = IGHD IGHD protein |
| 128. | IPI00010252 Gene_Symbol = TRIM33 Isoform Alpha of E3 ubiquitin-protein ligase TRIM33 |
| 129. | IPI00041065 Gene_Symbol = HABP2 Hyaluronan-binding protein 2 precursor |
| 130. | IPI00297550 Gene_Symbol = F13A1 Coagulation factor XIII A chain precursor |
| 131. | IPI00005439 Gene_Symbol = FETUB Fetuin-B precursor |
| 132. | IPI00064667 Gene_Symbol = CNDP1 Beta-Ala-His dipeptidase precursor |
| 133. | IPI00018305 Gene_Symbol = IGFBP3 Insulin-like growth factor-binding protein 3 precursor |
| 134. | IPI00023019 Gene_Symbol = SHBG Isoform 1 of Sex hormone-binding globulin precursor |
| 135. | IPI00382748 Gene_Symbol = HYI Isoform 3 of Putative hydroxypyruvate isomerase |
| 136. | IPI00004798 Gene_Symbol = CRISP3 Cysteine-rich secretory protein 3 precursor |
| 137. | IPI00032956 Gene_Symbol = KIAA1166 Isoform 1 of Hepatocellular carcinoma-associated antigen 127 |
| 138. | IPI00022434 Gene_Symbol = ALB Uncharacterized protein ALB |
| 139. | IPI00009276 Gene_Symbol = PROCR Endothelial protein C receptor precursor |
| 140. | IPI00030739 Gene_Symbol = APOM Apolipoprotein M |
| 141. | IPI00032311 Gene_Symbol = LBP Lipopolysaccharide-binding protein prec |

The invention claimed is:

1. A method of assaying for an analyte, comprising:
   a) covalently, labelling a test sample comprising the analyte with one or more isobaric mass labels to provide labeled test sample;
   b) covalently labelling a calibration sample comprising at least two different aliquots of the analyte, each analyte aliquot having a different known quantity of the analyte, with two or more isobaric mass labels to provide labeled calibration sample; wherein the test sample and each analyte aliquot of the calibration sample are differentially labelled with one or more isobaric mass labels, each with a mass spectrometrically distinct mass marker group, such that the test sample and each analyte aliquot of the calibration sample can be distinguished by mass spectrometry;
   c) combining the labeled test sample with the labeled calibration sample;
   d) determining by mass spectrometry the quantity of the analyte in the test sample and the quantity of analyte in each analyte aliquot in the calibration sample, and calibrating the quantity of the analyte in the test sample against the known and determined quantities of the analytes in the aliquots in the calibration sample.

2. The method according to claim 1, wherein the test sample comprises a plurality of different analytes and a calibration sample is provided for each different analyte, and wherein step (d) is repeated for each different analyte, wherein the plurality of analytes are peptide fragments of a protein or polypeptide which are produced by chemical or enzymatic processing of the protein or polypeptide prior to step (c), and/or wherein the at least two different aliquots of each calibration sample are selected such that each calibration sample provides a range of quantities of the analyte which are different to the range of quantities of analyte in a calibration sample for a different analyte; and
   wherein the aliquots are taken from a sample which is a standardized form of the test sample.

3. The method according to claim 1, wherein a plurality of test samples are assayed for an analyte, wherein each of the plurality of test samples is assayed for the same analyte, and/or wherein each of the test samples is differentially labelled with one or more of the isobaric mass labels and combined with the calibration sample in step (c), and the quantity of the analyte in each sample is determined simultaneously in step (d), or alternatively wherein each test sample is labelled with the same mass label, and steps (c) and (d) are repeated for each different sample, wherein the same calibration sample is used for each test sample to be assayed.

4. The method according to claim 1, wherein the method comprises a further step of combining the differentially labelled aliquots to produce a calibration sample prior to step (c).

5. The method according to claim 1, wherein step (d) comprises:
   i) in a mass spectrometer selecting and fragmenting ions of a mass to charge ratio corresponding to the analyte labelled with the mass label, detecting and producing a mass spectrum of fragment ions, and/or identifying the fragment ions corresponding to the mass marker groups of the mass labels;
   ii) determining the quantity of the analyte in each test sample on the basis of the quantity of their mass marker groups in a mass spectrum relative to the quantities of the mass marker groups from the aliquots of the calibration sample in the same mass spectrum.

6. The method according to claim 1, wherein the quantity of an analyte in each aliquot in the calibration sample is a known absolute quantity, wherein the absolute quantity of an analyte in a test sample is determined in step (d).

7. The method according to claim 1, wherein the quantity of analyte in each aliquot in the calibration sample is a known qualitative quantity, wherein the qualitative quantity is an expected range of quantities of analyte in a subject having a particular state, and/or wherein the calibrating step comprises calibrating the quantity of the analyte in the test sample against the known qualitative and determined quantities of the analytes in the aliquots of the calibration sample, wherein the percentage change in the amount of the analyte in the test sample is determined.

8. The method according to claim 1, wherein the quantity of analyte in each different aliquot is selected to reflect the known or suspected variation in the quantity of the analyte in the test sample, preferably wherein aliquots are provided which comprise the analyte in quantities which correspond to the upper and lower limits, and optionally intermediate points within a range of the known or suspected quantities of the analyte found in test samples of healthy or diseased subjects.

9. The method according to claim 1, wherein the different quantities of analyte present in the different aliquots correspond to the known or suspected quantity of analyte present in a test sample which has been incubated for different periods of time.

10. The method according to claim 1, wherein the test sample and/or the aliquots of the calibration sample are from a plant or an animal, wherein the animal is a human.

11. The method according to claim 1, wherein the calibration sample comprises an analyte in a quantity that indicates the efficacy and/or toxicity of a therapy, and/or wherein the test sample and/or the calibration sample comprises human or animal tissue, blood, plasma, serum, cerebrospinal fluid, synovial fluid, ocular fluid, urine, tears, tear duct exudates, lung aspirates, breast milk, nipple aspirate, semen, lavage fluid, cell extract, tissue culture extract, plant tissue, plant fluid, plant cell culture extract, a bacterial sample, a virus sample, fungus, fermentation broth, a foodstuff or a pharmaceutical composition, and/or wherein the analyte comprises a protein, a polypeptide, a peptide, an amino acid or a nucleic acid, a peptide-nucleic acid, a sugar, starch, a complex carbohydrate, a lipid, a polymer, or fragments thereof.

12. The method according to claim 1, which further includes the step of separating the isobarically labelled analytes electrophoretically or chromatographically after step (c) but before step (d).

13. The method according to claim 1, wherein the calibration sample comprises a further aliquot which comprises the analyte in a quantity which serves as a trigger during a mass spectrometric scan or during non-scanning tandem mass spectrometry to initiate a tandem mass spectrometry scan, wherein the analyte in the further aliquot is labelled with an isobaric mass label, or alternatively wherein the analyte in the further aliquot is labelled with a mass label which is chemically identical to but isotopically distinct and differing in mass from the isobaric mass labels of the other analytes in the calibration sample.

14. The method according to claim 1, wherein the analyte in the sample is a protein, and the analyte in the calibration sample is a recombinant form of the protein in the sample.

15. The method according to claim 1, wherein the mass label comprises the following structure:

X-L-M wherein X is a mass marker moiety comprising the following group:

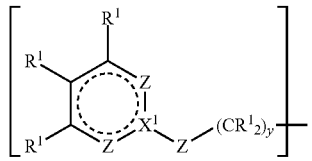

wherein the cyclic unit of the mass marker moiety is aromatic or aliphatic and comprises from 0-3 double bonds; each Z is independently N, N(R$^1$), C(R$^1$), CO, CO(R$^1$), C(R$^1$)$_2$, O or S; X$^1$ is N, C or C(R$^1$); each R$^1$ is independently H, a substituted or unsubstituted straight or branched C$_1$-C$_6$ alkyl group, a substituted or unsubstituted aliphatic cyclic group, a substituted or unsubstituted aromatic group or a substituted or unsubstituted heterocyclic group; and y is an integer from 0-10, L is a cleavable linker and M is a mass normalization moiety, wherein the cleavable linker attaching the mass marker moiety to the mass normalization moiety is a linker cleavable by Collision Induced Dissociation (CID), Electron Transfer Dissociation (ETD), Electron Capture Dissociation (ECD) or Surface Induced Dissociation (SID) using mass spectrometry.

16. The method according to claim 4, wherein the labelling step comprises a step of reacting the analyte with a reactive mass label, wherein the reactive mass label comprises a mass label and a reactive functionality, wherein the reactive functionality is capable of reacting with any amino group on a polypeptide and comprises a nucleophile or an electrophile, and wherein the reactive functionality comprises the following group:

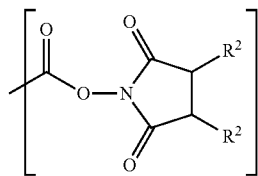

wherein each R$^2$ is independently H, a substituted or unsubstituted straight or branched C$_1$-C$_6$ alkyl group, a substituted or unsubstituted aliphatic cyclic group, a substituted or unsubstituted aromatic group or a substituted or unsubstituted heterocyclic group.

17. The method according to claim 15, wherein the mass label is a mass label from a set of two or more mass labels, wherein each mass normalization moiety ensures that a mass label has a desired aggregate mass, and wherein the set comprises:

mass labels having a mass marker moiety, each mass marker moiety having a mass different from that of all other mass marker moieties in the set, and each label in the set having a common aggregate mass, and wherein all the mass labels in the set are distinguishable from each other by mass spectroscopy, and wherein each mass label in the set has a mass adjuster moiety, selected from:

(a) an isotopic substituent situated within the mass marker moiety and/or within the mass normalization moiety, and (b) substituent atoms or groups attached to the mass marker moiety and/or attached to the mass normalization moiety, and/or wherein the mass adjuster moiety is selected from a halogen atom substituent, a methyl group substituent, and $^2$H, $^{15}$N, $^{13}$C, or $^{18}$O isotopic substituents.

18. The method according to claim 17, wherein the mass adjuster moiety is $^{15}$N or $^{13}$C and the set comprises two mass labels having the following structures:

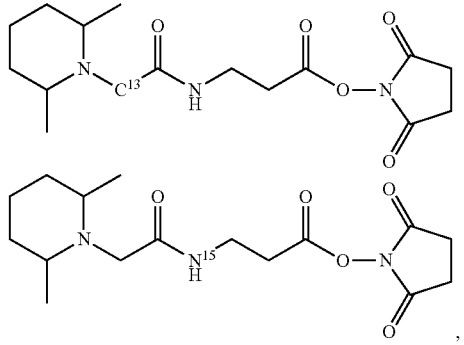

or five mass labels having the following structures:

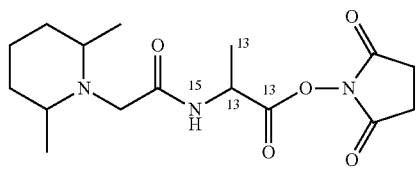

-continued
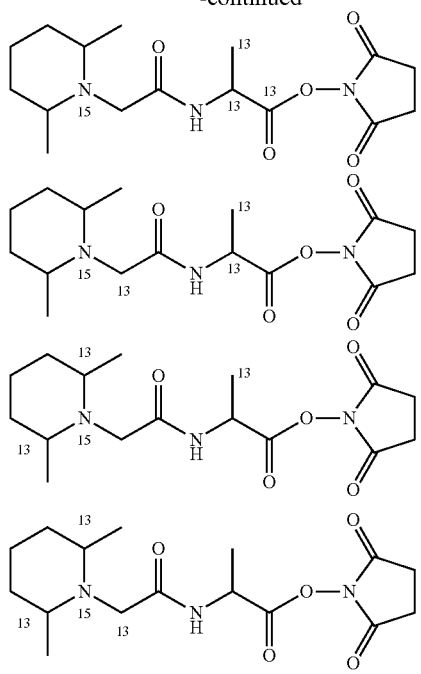
19. The method according to claim 17, wherein the mass adjuster moiety is $^{15}N$ and $^{13}C$ and the set comprises six mass labels having the following structures or stereoisomers of the following structures:
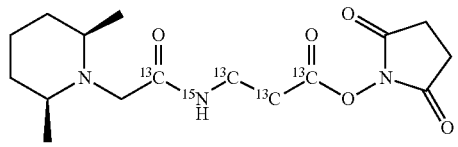
I
-continued
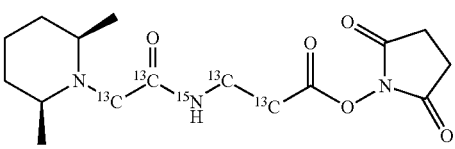
II
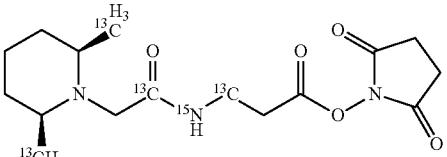
III
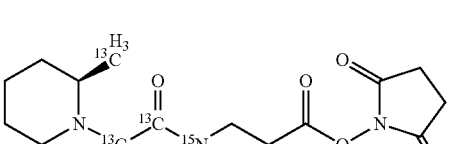
IV
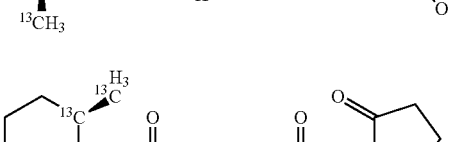
V
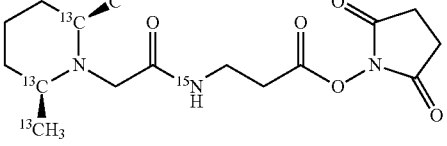
VI
* * * * *

SEQUENCE LISTING

```
<160> NUMBER OF SEQ ID NOS: 17

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Phe Gln Val Asp Asn Asn Asn Arg
1               5

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Ala Tyr Pro Leu Ser Ile Glu Pro Ile Gly Val Arg
1               5                   10

<210> SEQ ID NO 3
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 3

Gly Gln Tyr Cys Tyr Glu Leu Asp Glu Lys
1               5                   10

<210> SEQ ID NO 4
<211> LENGTH: 10
<212> TYPE: PRT
<213> ORGANISM: Bos taurus

<400> SEQUENCE: 4

Lys Ala Glu Phe Val Glu Val Thr Lys Leu
1               5                   10

<210> SEQ ID NO 5
<211> LENGTH: 7
<212> TYPE: PRT
<213> ORGANISM: Bos taurus

<400> SEQUENCE: 5

Lys Ala Phe Asp Glu Lys Leu
1               5

<210> SEQ ID NO 6
<211> LENGTH: 8
<212> TYPE: PRT
<213> ORGANISM: Bos taurus

<400> SEQUENCE: 6

Lys Ala Trp Ser Val Ala Arg Leu
1               5

<210> SEQ ID NO 7
<211> LENGTH: 17
<212> TYPE: PRT
<213> ORGANISM: Bos taurus

<400> SEQUENCE: 7

Lys Lys Val Pro Gln Val Ser Thr Pro Thr Leu Val Glu Val Ser Arg
1               5                   10                  15

Asn

<210> SEQ ID NO 8
<211> LENGTH: 15
<212> TYPE: PRT
<213> ORGANISM: Bos taurus

<400> SEQUENCE: 8

Lys Leu Gly Glu Tyr Gly Phe Gln Asn Ala Leu Ile Val Arg Tyr
1               5                   10                  15

<210> SEQ ID NO 9
<211> LENGTH: 12
<212> TYPE: PRT
<213> ORGANISM: Bos taurus

<400> SEQUENCE: 9

Lys Leu Val Asn Glu Leu Thr Glu Phe Ala Lys Thr
1               5                   10

<210> SEQ ID NO 10
```

```
<211> LENGTH: 9
<212> TYPE: PRT
<213> ORGANISM: Bos taurus

<400> SEQUENCE: 10

Lys Leu Val Thr Asp Leu Thr Lys Val
1               5

<210> SEQ ID NO 11
<211> LENGTH: 10
<212> TYPE: PRT
<213> ORGANISM: Bos taurus

<400> SEQUENCE: 11

Lys Gln Asn Cys Asp Gln Phe Glu Lys Leu
1               5                   10

<210> SEQ ID NO 12
<211> LENGTH: 11
<212> TYPE: PRT
<213> ORGANISM: Bos taurus

<400> SEQUENCE: 12

Lys Gln Thr Ala Leu Val Glu Leu Leu Lys His
1               5                   10

<210> SEQ ID NO 13
<211> LENGTH: 9
<212> TYPE: PRT
<213> ORGANISM: Bos taurus

<400> SEQUENCE: 13

Lys Val Leu Thr Ser Ser Ala Arg Gln
1               5

<210> SEQ ID NO 14
<211> LENGTH: 9
<212> TYPE: PRT
<213> ORGANISM: Bos taurus

<400> SEQUENCE: 14

Lys Tyr Leu Tyr Glu Ile Ala Arg Arg
1               5

<210> SEQ ID NO 15
<211> LENGTH: 23
<212> TYPE: PRT
<213> ORGANISM: Homo sapiens

<400> SEQUENCE: 15

Val Thr Thr Val Ala Ser His Thr Ser Asp Ser Asp Val Pro Ser Gly
1               5                   10                  15

Val Thr Glu Val Val Val Lys
            20

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 16

His His His His His His
```

-continued

```
1               5

<210> SEQ ID NO 17
<211> LENGTH: 8
<212> TYPE: PRT
<213> ORGANISM: Bos taurus

<400> SEQUENCE: 17

Ala Glu Phe Val Glu Val Thr Lys
1               5
```